(12) United States Patent
Cho et al.

(10) Patent No.: US 9,290,480 B2
(45) Date of Patent: Mar. 22, 2016

(54) QUINAZOLINE-2,4-DIONE DERIVATIVE, AND MEDICAL COMPOSITIONS FOR THE PROPHYLAXIS AND TREATMENT OF CRANIAL NERVE DISEASE CONTAINING THE SAME

(71) Applicants: Il Hwan Cho, Gyeonggi-do (KR); Eun Bang Lee, Seoul (KR); Sin Cheol Kang, Gyeonggi-do (KR); Won Seok Kim, Gyeonggi-do (KR); Chul Kyu Lee, Gyeonggi-do (KR)

(72) Inventors: Il Hwan Cho, Gyeonggi-do (KR); Eun Bang Lee, Seoul (KR); Sin Cheol Kang, Gyeonggi-do (KR); Won Seok Kim, Gyeonggi-do (KR); Chul Kyu Lee, Gyeonggi-do (KR)

(73) Assignee: Shin Poong Pharmaceuticals Co., Ltd., Gyeonggi-Do (KR)

( * ) Notice: Subject to any disclaimer, the term of this patent is extended or adjusted under 35 U.S.C. 154(b) by 88 days.

(21) Appl. No.: 13/710,543

(22) Filed: Dec. 11, 2012

(65) Prior Publication Data

US 2013/0102622 A1 Apr. 25, 2013

Related U.S. Application Data

(63) Continuation of application No. 12/863,332, filed as application No. PCT/KR2009/000083 on Jan. 8, 2009, now Pat. No. 8,404,696.

(30) Foreign Application Priority Data

Jan. 30, 2008 (KR) .................. 10-2008-0009390

(51) Int. Cl.
*C07D 239/96* (2006.01)
*C07D 403/12* (2006.01)

(52) U.S. Cl.
CPC .................. *C07D 403/12* (2013.01)

(58) Field of Classification Search
USPC ................. 514/266.1, 266.2; 544/283, 284
See application file for complete search history.

(56) References Cited

FOREIGN PATENT DOCUMENTS

| WO | 2008/112715 A2 | 9/2008 |
|---|---|---|
| WO | 2009096667 | 8/2009 |

OTHER PUBLICATIONS

International Search Report from PCT/KR09/000083 maiied Aug. 18, 2009.
Floyd, Robert A. Antioxidants, Oxidative Stress, and Degenerative Neurological Disorders. Antioxidants, Oxidative Stress, and Neural Disorders. Proceedings of the Society for Experimental Biology and Medicine. Dec. 1999. 236-245, vol. 222, issue 3. Society for Experimental Biology and Medicine, New York, NY.
Martin, Henry G.S. and Wang, Yu T., Blocking the Deadly Effect of the NMDA Receptor in Stroke, Cell (2010) 140:2, 174-76.
(Abstract) Mueller et al., NPS 1506, a novel NMDA receptor antagonist and neuroprotectant. Review or preclinical and clinical studies, Ann N.Y. Acad. Sci. (1999), 890:450-7.
(Abstract) Ghasemi, Mehdi and Schachter, Steven C., The NMDA receptor complex as a therapeutic target in epilepsy: a review, Epilepsy & Behavior (2011), 22:4, 617-40.
(Abstract) Olivares et al., N-methy-D-aspartate receptor antagonists and memantine treatment for Alzheimer's disease, vascular dementia and Parkinson's disease, Current Alzheimer Research (2012), 9(6):746-58.
Su-Jin Noh et al., "SP-8203 reduces oxidative stress via SOD activity and behaviorial deficit in cerebral ischemia", Pharmacology, Biochemistry and Behavior 98 (2011) 150-154.

*Primary Examiner* — Paul V. Ward
(74) *Attorney, Agent, or Firm* — Clark G. Sullivan; Troutman Sanders LLP (57) ABSTRACT

The present invention relates to a novel quinazoline-2,4-dione derivative of formula (I), a pharmaceutically acceptable salt thereof, and a pharmaceutical composition comprising a compound of formula (I) as an active ingredient for preventing or treating neurological brain disease.

15 Claims, 1 Drawing Sheet

QUINAZOLINE-2,4-DIONE DERIVATIVE, AND MEDICAL COMPOSITIONS FOR THE PROPHYLAXIS AND TREATMENT OF CRANIAL NERVE DISEASE CONTAINING THE SAME

TECHNICAL FIELD

The present invention relates to a novel quinazoline-2,4-dione derivative of formula (I)

(I)

wherein
$R_1$ is hydrogen or alkyl;
each of $R_2$ and $R_3$ is independently selected from hydrogen, alkyl, $-COR_6$, $-SO_2R_7$, or substituted or unsubstituted phenyl or benzyl, wherein $R_6$ is alkyl, alkoxy, phenyl, phenyloxy or benzyloxy, each of which is unsubstituted or substituted with halogen, hydroxy, methoxy, ethoxy or nitro, and $R_7$ is unsubstituted or substituted lower alkyl or aryl;
A is $-(CH_2)_n-$ or $-CH_2CH=CHCH_2-$, wherein n is an integer selected from 2 to 4;
$R_4$ is hydrogen and $R_5$ is hydrogen or benzoyl unsubstituted or substituted with one or more of halogen, hydroxy, alkoxy or nitro in benzene ring or when $R_4$ and $R_5$ together with N form a ring, $R_4$ and $R_5$ form a divalent moiety of wherein $R_8$ is hydrogen or alkyl;
each of l and m is independently an integer selected from 2 to 4; and
p is an integer of 0 or 1,
or a pharmaceutically acceptable salt thereof, and a pharmaceutical composition comprising the compound of formula (I) as an active ingredient for preventing or treating neurological brain diseases

BACKGROUND ART

Neurological brain diseases progress by the death of nerve cells for a short or long time and result in fatal loss of brain function. Stroke is one of the cerebrovascular diseases most frequently generated. Because cranial nerve disorders in patients in the vigorous age group from the forties to fifties have remarkably increased, it is pointed out as not only an individual issue but also a national issue.

There are largely two kinds of stroke: cerebral infarction and cerebral hemorrhage. Cerebral infarction results from necrosis of brain tissue caused by a blockage of blood supply to brain tissue brought on by thrombus and so forth. Cerebral hemorrhage, on the other hand, results from loss of blood due to ruptured blood vessels in the brain. Although the pathogeneses of cerebral infarction and cerebral hemorrhage are different, their symptoms are often similar.

The standard method for treating the acute period of infarction is currently thrombolysis. The time period before starting treatment and after onset of cerebral infarction is very important, and it is known that the patient's functional status can be improved when a thrombolytic agent is administrated within 3 hours after onset of cerebral infarction.

The cause of brain cell necrosis due to ischemia has been elucidated by many researchers, and the main pathway is suggested as excitable toxicity by excessive neurotransmitter, oxidative toxicity by stress, zinc toxicity, apoptosis and so forth.

Glutamate, which is one of the excitable toxic substances, is an excitable neurotransmitter of the central nervous system, and it reacts with NMDA (N-methyl-D-aspartate) receptor. Death of nerve cells is induced when glutamate is overproduced by ischemia. It is recently reported that these excitable toxicities may be the main mechanism of nerve cell's death by ischemic stroke as well as epilepsy. If the supply of oxygen-glucose to nervous tissue after ischemia is reduced, glutamate which is an excitable neurotransmitter, is accumulated in the junction between neurons. And then, nerve cell's death by excessive activity of NMDA glutamate receptor mainly occurs. Therefore, nerve cell's death by ischemic stroke can be suppressed by using antagonist of NMDA glutamate receptor.

Free radicals are also one of the main mechanisms of nerve cell death. An increase of free radicals by ischemia and others in nerve cells induces destruction of membrane lipid by lipid peroxidation, damage of nucleic acid by oxygen radicals, denaturation of protein and the like. This results in fatal damage to essential factors for cell survival. Many researchers have reported that ischemia leads to increases of active oxygen in the brain, reactive oxygen species in Parkinson's disease, Huntington's disease and Alzheimer's disease, catalase (a radical-scavenging enzyme), activity of Cu/Zn superoxide dismutase (SOD) and $Fe^{2+}$.

As mentioned above, although many mechanisms are revealed to treat cranial nerve disorders, development of new drugs is delayed because of problems about efficacy and toxicity.

The present inventors found out that natural substances are released from living *Eisenia Andrei* and *Eisenia fetida* given electrostimulation while we studied them from folk remedies long used in the Orient. And we discovered that specific compounds of these substances show the valid protection of cranial nerves. Many derivative compounds including new compounds isolated from natural products were synthesized based on this discovery. It was learned that quinazoline-2,4-dione derivative compound of formula (I) and a salt thereof have a superior effect on protecting the activity of nerve cells, and we perfected the present invention.

DETAILED DESCRIPTION OF THE INVENTION

Purpose of the Invention

The purpose of the present invention is to provide a compound of formula (I) or a pharmaceutically acceptable salt thereof, and a pharmaceutical composition comprising said compound as an active ingredient for preventing or treating neurological brain diseases.

Technical Means

The present invention provides a novel quinazoline-2,4-dione derivative of formula (I)

(I)

wherein
$R_1$ is hydrogen or alkyl;
each of $R_2$ and $R_3$ is independently selected from hydrogen, alkyl, —$COR_6$, —$SO_2R_7$, or substituted or unsubstituted phenyl or benzyl, wherein $R_6$ is alkyl, alkoxy, phenyl, phenyloxy or benzyloxy, each of which is unsubstituted or substituted with halogen, hydroxy, methoxy, ethoxy or nitro, and $R_7$ is unsubstituted or substituted lower alkyl or aryl;
A is —$(CH_2)_n$— or —$CH_2CH=CHCH_2$—, wherein n is an integer selected from 2 to 4;
$R_4$ is hydrogen and $R_5$ is hydrogen or benzoyl unsubstituted or substituted with one or more of halogen, hydroxy, alkoxy or nitro in benzene ring or when $R_4$ and $R_5$ together with N form a ring, $R_4$ and $R_5$ form a divalent moiety of wherein $R_8$ is hydrogen or alkyl;
each of l and m is independently an integer selected from 2 to 4; and
p is an integer of 0 or 1,
or a pharmaceutically acceptable salt thereof.

As used herein, the term "alkyl" refers to alkyl having from 1 to 6 carbon atoms, for example, an aliphatic hydrocarbon chain including straight chain, branched chain or cyclic form such as methyl, ethyl, n-propyl, isopropyl, n-butyl, sec-butyl, isobutyl, tert-butyl, n-pentyl, 2-methylpentyl, hexyl and cyclohexyl.

The term "lower alkyl" refers to a straight or branched hydrocarbon chain having from 1 to 4 carbon atoms.

The term "alkoxy" refers to —O-alkyl, wherein "alkyl" refers to a straight or branched hydrocarbon chain having from 1 to 4 carbon atoms.

The compounds of formula (I) can be used in forms of pharmaceutically acceptable salts thereof and the pharmaceutically acceptable salts include conventionally known acid addition salts or alkali metal salts in the art.

Typical examples of formula (I) according to the present invention are as follows:

3-{3-[4-(3-aminopropylamino)butylamino]propyl}-1H-quinazoline-2,4-dione;
3-(3-{4-[3-(2,4-dioxo-4-dihydro-2H-quinazolin-3-yl)propylamino]butylamino}propyl)-1H-quinazoline-2,4-dione;
N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}acetamide;
N-(4-{acetyl-[3-(2,4-dioxo-1,4-dihydro-2H-quinazolin-3-yl)propyl]amino}butyl)-N-[3-(2,4-dioxo-1,4-dihydro-2H-quinazolin-3-yl)propyl]acetamide;
[3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid ethyl ester;
N-[3-(2,4-dioxo-1,4-dihydro-2H-quinazolin-3-yl)propyl]-N-(4-{[3-(2,4-dioxo-1,4-dihydro-2H-quinazolin-3-yl)propyl]methylamino}butyl)acetamide;
3-{4-[3-(2,4-dioxo-1,4-dihydro-2H-quinazolin-3-yl)propylamino]butyl}-1H-quinazoline-2,4-dione;
N-(3-{4-[3-(2,4-dioxo-1,4-dihydro-2H -quinazolin-3-yl)propylamino]butylamino}propyl)-4-hydroxybenzamide;
3-{3-[4-({N-[3-(2,4-dioxo-1,4-dihydro-2H-quinazolin-3-yl)propyl]-N-benzyl}amino)butylamino]propyl}-1H-quinazoline-2,4-dione;
N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}benzamide;
[3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid tert-butyl ester;
N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}methansulfonamide;
N-(4-{benzyl-[3-(2,4-dioxo-1,4-dihydro-2H-quinazolin-3-yl)propyl]amino}butyl)-N-[3-(2,4-dioxo-1,4-dihydro-2H-quinazolin-3-yl)propyl]acetamide;
(4-{acetyl-[3-(2,4-dioxo-1,4-dihydro-2H-quinazolin-3-yl)propyl]amino}butyl)-[3-(2,4-dioxo-1,4-dihydro-2H-quinazolin-3-yl)propyl]carbamic acid ethyl ester;
3-{[3-(4-{N-[3-(2,4-dioxo-1,4-dihydro-2H-quinazolin-3-yl)propyl]-N-benzylamino}butyl)-N-benzylamino]propyl}-1H-quinazoline-2,4-dione;
[3-(2,4-dioxo-1,4-dihydro-2H-quinazolin-3-yl)propyl]-(4-{[3-(2,4-dioxo-1,4-dihydro-2H-quinazolin-3-yl)propyl]ethoxycarbonylamino}butyl)carbamic acid ethyl ester;
(4-{tert-butoxycarbonyl-[3-(2,4-dioxo-1,4-dihydro-2H-quinazolin-3-yl)propyl]amino}butyl)-[3-(2,4-dioxo-1,4-dihydro-2H-quinazolin-3-yl)propyl]carbamic acid tert-butyl ester;
N-[3-(2,4-dioxo-1,4-dihydro-2H-quinazolin-3-yl)propyl]-N-(4-{[3-(2,4-dioxo-1,4-dihydro-2H-quinazolin-3-yl)propyl]methansulfonylamino}butyl)methansulfonamide;
N-[3-(acetyl-{4-[3-(2,4-dioxo-1,4-dihydro-2H-quinazolin-3-yl)propylamino]butyl}amino)propyl]-4-hydroxybenzamide;
N-[3-(4-{acetyl-[3-(2,4-dioxo-1,4-dihydro-2H-quinazolin-3-yl)propyl]amino}butylamino)propyl]-4-hydroxybenzamide;
N-{3-[acetyl-(4-{acetyl-[3-(2,4-dioxo-1,4-dihydro-2H-quinazolin-3-yl)propyl]amino}butyl)amino]propyl}-4-hydroxybenzamide;
N-[4-(2,4-dioxo-1,4-dihydro-2H-quinazolin-3-yl)butyl]-N-[3-(2,4-dioxo-1,4-dihydro-2H-quinazolin-3-yl)propyl]acetamide;

3-(2-{3-[2-(2,4-dioxo-1,4-dihydro-2H-quinazolin-3-yl)ethylamino]propylamino}ethyl)-1H-quinazoline-2,4-dione;
3-(3-{3-[3-(2,4-dioxo-1,4-dihydro-2H-quinazolin-3-yl)propylamino]propylamino}propyl)-1H-quinazoline-2,4-dione;
3-(3-{4-[3-(2,4-dioxo-1,4-dihydro-2H-quinazolin-3-yl)propylamino]-2-butenylamino}propyl)-1H-quinazoline-2,4-dione;
(4-{tert-butoxycarbonyl-[3-(1-methyl-2,4-dioxo-1,4-dihydro-2H-quinazolin-3-yl)propyl]amino}butyl)-[3-(1-methyl-2,4-dioxo-1,4-dihydro-2H-quinazolin-3-yl)propyl]carbamic acid tert-butyl ester;
1-methyl-3-(3-{4-[3-(1-methyl-2,4-dioxo-1,4-dihydro-2H-quinazolin-3-yl)propylamino]butylamino}propyl)-1H-quinazoline-2,4-dione;
3-(3-{-4-[3-(1,3-dioxo-1,3-dihydro-isoindole-2-yl)propylamino]butylamino}propyl)-1H-quinazoline-2,4-dione;
3-(3-{2-[3-(2,4-dioxo-1,4-dihydro-2H-quinazolin-3-yl)propylamino]ethylamino}propyl)-1H-quinazoline-2,4-dione;
[3-(2,4-dioxo-1,4-dihydro-2H-quinazolin-3-yl)propyl]-(4-{[3-(2,4-dioxo-1,4-dihydro-2H-quinazolin-3-yl)propyl]hexylamino}butyl)carbamic acid tert-butyl ester;
3-[3-(4-{N-[3-(2,4-dioxo-1,4-dihydro-2H-quinazolin-3-yl)propyl]-N-hexylamino}butylamino)propyl]-1H-quinazoline-2,4-dione;
(4-{tert-butoxycarbonyl-[3-(1-hexyl-2,4-dioxo-1,4-dihydro-2H-quinazolin-3-yl)propyl]amino}butyl)-[3-(1-hexyl-2,4-dioxo-1,4-dihydro-2H-quinazolin-3-yl)propyl]carbamic acid tert-butyl ester;
1-hexyl-3-(3-{4-[3-(1-hexyl-2,4-dioxo-1,4-dihydro-2H-quinazolin-3-yl)propylamino]butylamino}propyl)-1H-quinazoline-2,4-dione;
[3-(2,4-dioxo-1,4-dihydro-2H-quinazolin-3-yl)propyl]-(4-{[3-(2,4-dioxo-1,4-dihydro-2H-quinazolin-3-yl)propyl]heptanoylamino}butyl)carbamic acid tert-butyl ester;
[3-(2,4-dioxo-1,4-dihydro-2H-quinazolin-3-yl)propyl]-{4-[3-(2,4-dioxo-1,4-dihydro-2H-quinazolin-3-yl)propylamino]butyl}heptanoic amide;
N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-2,2,2-trifluoroacetamide;
N-[3-(2,4-dioxo-1,4-dihydro-2H-quinazolin-3-yl)propyl]-N-{4-[[3-(2,4-dioxo-1,4-dihydro-2H-quinazolin-3-yl)propyl]-(2,2,2-trifluoroacetyl)amino]butyl}-2,2,2-trifluoroacetamide;
N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-2-methoxyacetamide;
[3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid benzyl ester;
N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-4-methylbenzenesulfonamide;
N-[3-(2,4-dioxo-1,4-dihydro-2H-quinazolin-3-yl)propyl]-N-(4-{[3-(2,4-dioxo-1,4-dihydro-2H-quinazolin-3-yl)propyl]-4-methylbenzenesulfonylamino}butyl)-4-methylbenzenesulfonamide; or
3-(3-{4-[3-(2,5-dioxo-pyrrolidine-1-yl)propylamino]butylamino}propyl)-1H-quinazoline-2,4-dione.

The compound of formula (1) can be prepared by the reactions as described in the following reaction schemes I to III. Therefore, it is another object of the present invention to provide such preparation processes.

However, the following reaction schemes illustrate most general preparation processes of the present invention. The processes for preparing the compound of formula (1) according to the present invention are not limited to the following illustrated reaction schemes. The compound of formula (1) can be prepared by various processes known in the arts.

Reaction scheme I

By reacting the benzoic acid derivative compound (IV) having an alkoxycarbonylamino substituent at position 2 with amine compound (V) in which A is suitably selected to form a ring under the existence or the absence of solvent, a quinazoline 2,4-dione derivative of primary amine compound (IX) having a quinazoline 2,4-dione skeleton structure may be obtained, wherein $R_4$ and $R_5$ are hydrogens. Alternatively, by increasing stoichiometric amounts of the compound (1V), a quinazoline 2,4-dione derivative of compounds (IX) in which $R_4$ and $R_5$ form cyclic quinazoline-2,4-dione with N atom may be obtained. Ring fusion reaction under the absence of solvents should be carried out at a temperature sufficient to melt two reactants.

In the above reaction scheme, A, l, m and p are the same as defined above, $R_4$ and $R_5$ represent hydrogens, or when $R_4$ and $R_5$ together with N form a ring, $R_4$ and $R_5$ form a divalent moiety of and Alk represents alkyl. L represents a leaving group that is preferably hydroxy, alkoxy or halogen.

Reaction scheme II

By the reaction of the compound (VI) with the compound (VII) or (VIII) having $R_4$ and $R_5$ substituents, a quinazoline-2,4-dione derivative of the compound (IX) in which $R_4$ and $R_5$ are suitably introduced into terminal primary amine may be obtained, wherein the reaction may be carried out under the existence of solvents, fusion reaction may be carried out under the absence of solvents or condensation reaction may be carried out, if X is hydroxy.

The condensation reaction may be carried out by using DCC (dicyclohexyl carbodiimide) or EDC (1-(3-dimethylaminopropyl)-3-ethyl-carbodiimide). Alternatively, the compound (IX) may be obtained by conversing carboxyl group into more reactive group such as acid anhydride or acid chloride and then reacting it with the compound (VI).

In the above reaction scheme, A, $R_4$, $R_5$, l, m and p are the same as defined above, $R_5$ is not H, X represents hydroxy, halogen, alkoxy or —$OR_5$, Each of Y and Y' is hydroxy, halogen, alkoxy or when Y and Y' form a ring, Y and Y' form —O—.

Reaction scheme III

By substituting at least one hydrogen of the compound of formula (IX) with $R_2$ and/or $R_3$, a quinazoline-2,4-dione derivative of the compound (I) may be obtained, wherein $R_2$ and $R_3$ are suitably introduced into amine position, $R_1$ is hydrogen, and at least one of $R_2$ and $R_3$ is not hydrogen. In case of obtaining the compound in which $R_2$ and $R_3$ are the same substituents, $R_2$ and $R_3$ substituents can be introduced at once.

In case of obtaining the compound in which $R_2$ and $R_3$ are different substituents, $R_2$ substituent can be first introduced into the compound (IX) to obtain the quinazoline-2,4-dione derivative of the compound (I) that $R_1$ and $R_3$ are hydrogen, and then $R_3$ substituent can be introduced in the presence of organic solvent and base. On the other hand, $R_3$ substituent can be first introduced into compounds (IX) and then $R_2$ substituent can be introduced into the $R_3$ substituted compound to obtain the quinazoline-2,4-dione derivative of the compound (1) in which $R_2$ and $R_3$ are suitably substituted and $R_1$ is hydrogen.

Also, after the desired substituents are introduced into the secondary amine position of the compound (IX), the quinazoline-2,4-dione derivative of the compound (I), in which $R_1$ is alkyl and the desired substituents are introduced, can be obtained by alkylation of position 1 in quinazoline ring with an alkylating agent under the existence of base or additional deprotection subsequent to the alkylation. Alkyl halide, dialkyl sulfate or alkyl sulfonate can be used as the above alkylating agent.

In the above reaction scheme, A, $R_1$, $R_2$, $R_3$, $R_4$, $R_5$, l, m and p are the same as defined above, and $R_5$ is not H. More specific reaction conditions are described in the following Examples 1 to 42.

On the other hand, the compound of formula (1) according to the present invention prepared by the above processes can be subjected to further isolation and purification by conventional post-treatment methods or can be prepared as a corresponding, pharmaceutically acceptable salt by conventional methods. The salt, as generally known to skilled artisans, should be pharmaceutically acceptable and not toxic. Several salts can be used to produce the compound of the present invention and a non-toxic, pharmaceutically acceptable salt thereof.

The pharmaceutically acceptable salt of the compound according to the present invention includes acid addition salts or alkali metal salts. Such acid addition salt may be, but not limited thereto, a salt with hydrochloric acid, hydrobromic acid, hydroiodic acid, sulfuric acid, acetic acid, benzensulfonic acid, methanesulfonic acid, phosphoric acid, nitric acid, formic acid, propionic acid, succinic acid, glucolic acid, lactic acid, malic acid, orotic acid, nicotinic acid, adipic acid, tartaric acid, citric acid, ascorbic acid, maleic acid, benzoic acid, salicylic acid, fumaric acid, camsylic acid or carboxylic acid, and such alkali metal salt may be, but not limited thereto, a salt of sodium, potassium, lithium, magnesium or calcium.

Additionally, the present invention provides a pharmaceutical composition which is useful for preventing or treating neurological brain diseases as aforementioned by combining the quinazoline-2,4-dione derivative compound of formula (I) and the pharmaceutically acceptable salt thereof with a pharmaceutically acceptable carrier.

The compound of formula (I) according to the present invention is useful for treating a disease caused by normal or abnormal degeneration of the neurological brain system or protecting the nerve cells therefrom, as proven by the results of the following examples.

The present invention provides a pharmaceutical composition comprising the compound of formula (I) or a pharmaceutically acceptable salt thereof as an active ingredient with a pharmaceutically acceptable carrier, for preventing or treating neurological brain system disorder, degenerative neurological brain disease or nervous system dysfunction. More specifically, a pharmaceutical composition according to the present invention is useful for preventing or treating the disease which is selected from neurological dysfunction, failing memory, cerebrovascular insufficiency, local brain injury, focal brain trauma, diffuse brain trauma, spinal cord injury, cerebral ischemia, cerebral hemorrhage, ischemic stroke, hemorrhagic stroke, dementia, cerebral infarction, embolic occlusion, thrombotic occlusion, reperfusion following acute ischemia, transient ischemic attack, perinatal hypoxic-ischemic injury, cardiac arrest, intracranial hemorrhage, subarachnoid hemorrhage, cerebral aneurysm, Willis aneurysm, acute infantile hemiplegia, whiplash, shaken-infant syndrome, Alzheimer's disease, Pick's disease, diffuse Lewy body disease, progressive supranuclear palsy (Steel-Richardson syndrome), multi-system degeneration (Shy-Drager syndrome), chronic epileptic conditions associated with neurodegeneration, motor neuron diseases, amyotrophic lateral sclerosis, primary lateral sclerosis, degenerative ataxias, cortical basal degeneration, subacute sclerosing panencephalitis, Huntington's disease, Parkinson's disease, synucleinopathies, primary progressive aphasia, spinal muscular atrophy and spinobulbar muscular atrophy (Kennedy's disease), multiple sclerosis, Tay-Sach's disease, spastic paraplegia, prion disease, Creutzfeldt-Jakob disease, epilepsy, plexopathy or neuropathy; and for memory improvement.

The pharmaceutical composition of the present invention can be prepared by combining a compound of the present invention with a pharmaceutically acceptable inactive carrier in the form of solid or liquid and may be formulated into an appropriate pharmaceutically acceptable form for administration. The above formulation may be prepared in the form of immediate release or sustained release, which would be well known to a skilled artisan. The pharmaceutical composition may be formulated into tablets, pills, granules, powders, capsules, suspensions, syrups, elixirs, solutions, emulsions or injections for oral, intravenous or parenteral administration. The pharmaceutical composition may be formulated into tablets, capsules, powders, microgranules, sterilized solutions or suspensions for rectal administration or in the form of suppositories.

The above pharmaceutically acceptable carrier may include lactose, dextrose, sucrose, sorbitol, mannitol, xylitol, erythritol, malditol, starch, acacia gum, alginate, gelatin, calcium phosphate, calcium silicate, cellulose, methyl-cellulose, microcrystalline cellulose, polyvinylpyrrolidone, water, methylhydroxybenzoate, propylhydroxybenzoate, talc, magnesium stearate or mineral oils. Additionally, the above pharmaceutically acceptable carrier may include diluents or additives such as fillers, extenders, bonding agents, wetting agents, disintegrants, surfactants, etc.

The solid formulation for oral administration may be in the form of tablets, pills, powders, granules, capsules, etc. and may include at least one additive, for example, such as starch, calcium carbonate, sucrose, lactose and gelatin, or lubricants such as magnesium stearate, talc, etc. The liquid formulation for oral administration may be in the form of suspensions, solutions, emulsions, syrups, etc. and may include diluents such as water and liquid paraffin, wetting agents, sweeteners, aromatics or preservatives. The formulation for parenteral administration may be in the form of sterilized solutions, non-aqueous solvents, suspensions, emulsions, lyophilizations or suppositories. Non-aqueous solvents and suspensions include propylene glycol, polyethylene glycol, vegetable oils such as olive oil, injectable esters such as ethyloleate, etc. Witepsol, macrogol, tween 61, cacao oil, lauryn oil, glycerogellatin and the like as a carrier for suppositories may be used.

The desirable dose of the compound of formula (I) or the pharmaceutically acceptable salt thereof included in the pharmaceutical composition of the present invention varies depending on the condition, weight, age and gender of the subject, severity of the disease, drug form, and route and period of administration, and may be chosen by those skilled in the art. For example, it is generally recommended to administer at the amount ranging from 0.01 to 500 mg/kg, preferably, 0.1 to 100 mg/kg by weight/day of the compound of formula (I) or the pharmaceutically acceptable salt thereof, but it is not limited to this scope. A single dose may be administered or it may be divided into several times per day or week.

Additionally, the pharmaceutical composition of the present invention may include 0.001 to 50 weight %, preferably 0.1 to 50 weight % of the compound of formula (I) or the pharmaceutically acceptable salt thereof, on the basis of total weight of the composition, but it is not limited to this scope.

Advantageous Effects

A quinazoline-2,4-dione derivative, a pharmaceutically acceptable salt thereof and a composition comprising the quinazoline-2,4-dione derivative and the pharmaceutically acceptable salt thereof according to the present invention have effects on suppression of cell death in the brain, protection of nerve cells, anti-oxidation, anti-convulsion and relaxation of blood vessels, and thus are useful for preventing or treating the aforementioned various diseases for example, stroke, Alzheimer's disease and epilepsy as well as enhancing memory.

CONCRETE EMBODIMENTS FOR CARRYING OUT THE INVENTION

The present invention will be more specifically explained by reference to the following examples, which are provided by way of illustration and are not intended as limiting.

EXAMPLE 1

3-{3-[4-(3-aminopropylamino)butylamino]propyl}-1H-quinazoline-2,4-dione (Compound 1)

1) Preparation of ethyl 2-ethoxycarbonylamino benzoate

Ethyl 2-amino benzoate (20 g, 0.12 mol) was dissolved in 140 mL xylene and ethyl chloroformate (13.8 mL, 0.15 mol) was added thereto. After reacting under reflux for 3 hours, the solvent was removed by distillation under reduced pressure. 30 mL petroleum ether was added to the residue and cooled. The title compound of white solid (26 g, 90.5%) was obtained by gathering the formed solid through the filtration process and by concentration and crystallization of the filtered solution.

$^1$H NMR (CDCl$_3$): 10.51 (s,1H), 8.43 (dd,1H), 8.01 (dd, 1H), 7.51 (t,1H), 7.01 (t,1H), 4.37 (q,2H), 4.22 (q,2H), 1.40 (t,3H), 1.32 (t,3H);

2) Preparation of 3-{3-[4-(3-aminopropylamino) butylamino]propyl}-1H-quinazoline-2,4-dione:

Ethyl 2-ethoxycarbonylamino benzoate (8.0 g, 33.7 mmol) and N,N'-bis-(3-aminopropyl)butane-1,4-diamine (8.87 g, 43.8 mmol) were melted with heating. After stirring for 4 hours at 125-135° C., isopropylalcohol was added thereto and concentrated hydrochloric acid was added to form solid.

The solid obtained by the filtration process was dissolved in water and neutralized with sodium hydroxide aqueous solution. After removal of water by distillation under reduced pressure, silica gel column-chromatography of the remaining residue was performed to give the title compound in oil form (5.0 g, 43%).

$^1$H NMR (D$_2$O): 7.48 (dd,1H), 7.30 (t,1H), 6.83 (m,2H), 3.73 (t,2H), 2.59 (t,2H), 2.52 (t,2H), 2.46 (t,6H), 1.66 (m,2H), 1.56 (m,2H), 1.37 (m,4H);

EXAMPLE 2

3-(3-{4-[3-(2,4-dioxo-1,4-dihydro-2H-quinazolin-3-yl)propylamino]butylamino}propyl)-1H-quinazoline-2,4-dione (Compound 2)

(Process 1)

Ethyl 2-ethoxycarbonylamino benzoate (4.9 g, 20.6 mmol) and N,N'-bis-(3-aminopropyl)butane-1,4-diamine (2.1 g, 10.3 mmol) was melted with heating. After stirring for 5 hours at 125-135° C., 25 mL isopropylalcohol was added thereto to make a solid and dried under reduced pressure after filtration to give the title compound of white solid (3.3 g, 64%).

$^1$H NMR (CDCl$_3$): 8.05 (d,2H), 7.62 (t,2H), 7.22 (t,2H), 7.15 (d,2H), 4.11 (t,4H), 2.62 (m,8H), 1.94 (m,4H), 1.55 (s,4H);

(Process 2)

3-{3-[4-(3-aminopropylamino)butylamino]propyl}-1H-quinazoline-2,4-dione (2.1 g, 6.0 mmol) and ethyl 2-ethoxycarbonylamino benzoate (1.6 g, 6.6 mmol) was melted at 125-135° C. After 5 hours, 20 mL isopropylalcohol was added thereto to make a solid and dried under reduced pressure after filtration to give the title compound of white solid (2.2 g, 74%) which is the same as the compound obtained by Process 1.

EXAMPLE 3

Hydrochloride acid salt of N-[3-(2,4-dioxo-1,4-dihydro-2H-quinazolin-3-yl)propyl]-N-{4-[3-(2,4-dioxo-1,4-dihydro-2H-quinazolin-3-yl)propylamino] butyl}acetamide (Compound 3)

After 3-(3-{4-[3-(2,4-dioxo-1,4-dihydro-2H-quinazolin-3-yl)propylamino]butylamino}propyl)-1H-quinazoline-2,4-dione (3 g, 6.1 mmol) was dissolved in 60 mL pyridine, acetic anhydride (0.7 mL, 7.3 mmol) was added thereto. After 2 hours, pyridine was removed by distillation under reduced pressure. Dichloromethane and water were added to the remaining residue, and each layer was separated in the solution after the formed solid was removed by the filtration process. Concentrated hydrochloric acid was added to the aqueous layer, and pH was adjusted to 2-3. After removal of water by distillation under reduced pressure, silica gel column-chromatography of the remaining residue was performed to give the title compound (1.1 g, 32%).

$^1$H NMR (MeOD): 7.97 (m,2H), 7.61 (m,2H), 7.17 (m,4H), 4.14 (m,2H), 4.02 (m,2H), 3.47 (m,4H), 3.07 (m,4H), 2.12 (m,5H), 1.96 (m,2H), 1.73 (m,4H);

By treating compound 1.0 g of the above Example 3 with ion exchange resin, compound in base form, N-[3-(2,4-dioxo-1,4-dihydro-2H-quinazolin-3-yl)propyl]-N-{4-[3-(2,4-dioxo-1,4-dihydro-2H-quinazolin-3-yl)propylamino] butyl}acetamide (0.65 g) was obtained.

$^1$H NMR (MeOD): 7.89 (m,2H), 7.53 (m,2H), 7.5-7.01 (m,4H), 3.97 (m,4H), 3.40 (t,2H), 3.32 (q,2H), 2.54 (m,4H), 2.05 (d,3H), 1.94-1.83 (m,4H), 1.61-1.44 (m,4H);

EXAMPLE 4

N-(4-{acetyl-[3-(2,4-dioxo-1,4-dihydro-2H-quinazolin-3-yl)propyl]amino}butyl)-N-[3-(2,4-dioxo-1,4-dihydro-2H-quinazolin-3-yl)propyl]acetamide (Compound 4)

After 3-(3-{4-[3-(2,4-dioxo-1,4-dihydro-2H-quinazolin-3-yl)propylamino]butylamino}propyl)-1H-quinazoline-2,4-dione (2 g, 4.1 mmol) was dissolved in 50 mL pyridine, acetic anhydride (1.0 mL, 10.2 mmol) was added. After 2 hours, pyridine was removed by distillation under reduced pressure, and silica gel column-chromatography of the remaining residue was performed to give the title compound (2.1 g, 90%).

$^1$H NMR (DMSO-d$_6$): 11.40 (s,2H), 7.91 (m,2H), 7.63 (m,2H), 7.17 (m,4H), 3.86 (m,4H), 3.27 (m,8H), 1.95 (m,6H), 1.80 (m,4H), 1.43 (m,4H);

EXAMPLE 5

Hydrochloric acid salt of [3-(2,4-dioxo-1,4-dihydro-2H-quinazolin-3-yl)propyl]-{4-[3-(2,4-dioxo-1,4-dihydro-2H-quinazolin-3-yl)propylamino] butyl}carbamic acid ethyl ester (Compound 5)

3-(3-{4-[3-(2,4-dioxo-1,4-dihydro-2H-quinazolin-3-yl)propylamino]butylamino}propyl)-1H-quinazoline-2,4-dione (2 g, 4.11=01) was dissolved in 20 mL hexamethylphosphoramide with heating, cooled and ethyl chloroformate (0.4 mL, 4.1 mmol) was added thereto. After 2 hours, silica gel column-chromatography of the reaction mixture was performed to give the title compound of yellow solid (0.48 g, 20%)

$^1$H NMR (MeOD): 8.00 (t,2H), 7.63 (q,2H), 7.21 (q,2H), 7.14 (m,2H), 4.15 (t,2H), 4.09 (q,2H), 4.02 (t,2H), 3.36 (m,4H), 3.05 (m,4H), 2.10 (m,2H), 1.95 (m,2H), 1.71 (t,4H), 1.21 (bs,3H);

EXAMPLE 6

N-[3-(2,4-dioxo-1,4-dihydro-2H-quinazolin-3-yl)propyl]{[3-(2,4-dioxo-1,4-dihydro-2H-quinazolin-3-yl)propyl]methylamino}butyl)acetamide (Compound 6)

Hydrochloride acid salt of N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}acetamide (2 g, 3.5 mmol) was dissolved in 80 mL dichloromethane and 10 mL methanol. Triethylamine (0.45 g, 4.5 mmol) and paraformaldehyde (0.14 g, 4.5 mmol) was added thereto and stirred for 2 hours at room temperature. After concentration of the solvent, 40 mL methanol and sodium borohydride (0.76 g, 20.2 mmol) were added thereto and stirred for 15 hours. After removal of methanol by distillation under reduced pressure, silica gel column-chromatography of the remaining residue was performed to give the title compound of white solid (1.2 g, 62%).

$^1$H NMR (MeOD): 7.98 (m,2H), 7.60 (m,2H), 7.19 (m,2H), 7.11 (m,2H), 4.02 (m,4H), 3.46-3.36 (m,4H), 2.69-2.52 (m,4H), 2.41, 2.34 (s,3H), 2.10 (d,3H), 1.98-1.90 (m,4H), 1.63-1.51 (m,41-1);

EXAMPLE 7

3-{4-[3-(2,4-dioxo-1,4-dihydro-2H-quinazolin-3-yl) propylamino]butyl}-1H-quinazoline-2,4-dione (Compound 7)

Ethyl 2-ethoxycarbonylamino benzoate (7 g, 29.5 mmol) and N-(3-aminopropyl)butane-1,4-diamine 2.1 g (14.8 mmol) were melted at 140° C. After 3 hours, 50 mL isopropylalcohol was added thereto for solid formation, filtered and dried under reduced pressure. The title compound of yellow solid was obtained (3.2 g, 50%).

$^1$H NMR (DMSO-$d_6$): 7.91 (m,2H), 7.63 (m,2H), 7.18 (m,4H), 3.90 (m,4H), 2.50 (m,4H), 1.69 (m,2H), 1.58 (m,2H), 1.39 (m,2H);

EXAMPLE 8

Dihydrochloric acid salt of N-(3-{4-[3-(2,4-dioxo-1, 4-dihydro-2H-quinazolin-3-yl)propylamino] butylamino}propyl)-4-hydroxybenzamide (Compound 8)

4-hydroxybenzoic acid (1.13 g, 8.2 mmol), 1-hydroxybenzotriazole (1.27 g, 9.4 mmol), 1,3-dicyclohexylcarbodiimide (1.94 g, 9.4 mmol) and N,N'-diisopropylethylamine (1.64 mL, 9.4 mmol) were added in 20 mL dimethylsulfoxide and stirred for 15 minutes. 3-{3-[4-(3-aminopropylamino)butylamino]propyl}-1H-quinazoline-2,4-dione (2.18 g, 6.3 mmol) dissolved in dimethylsulfoxide 10 mL was added thereto and stirred at 50° C. with heating. After 5 hours, dimethylsulfoxide was removed, the remaining solution was dissolved in methanol with concentrated hydrochloric acid. After the removal of methanol, silica gel column-chromatography of the remaining residue was performed to give the title compound of white solid (1.6 g, 47%).

$^1$H NMR ($D_2O$): 7.91 (d,1H), 7.74 (t,1H), 7.63 (d,2H), 7.33 (t,1H), 7.16 (d,1H), 6.87 (d,2H), 4.07 (t,2H), 3.53 (t,2H), 3.20 (m,8H), 2.11 (m,4H), 1.91 (s,4H);

EXAMPLE 9

3-{3-[4-({N-[3-(2,4-dioxo-1,4-dihydro-2H-quinazolin-3-yl)propyl]-N-benzyl}amino)butylamino]propyl}-1H-quinazoline-2,4-dione (Compound 9)

3-(3-{4-[3-(2,4-dioxo-1,4-dihydro-2H-quinazolin-3-yl) propylamino]butylamino}propyl)-1H-quinazoline-2,4-dione (2 g, 4.1 mmol) was dissolved in 60 mL tetrahydrofuran and sodium hydroxide (0.3 g, 8.1 mol) aqueous solution 60 mL and was cooled. Benzyl bromide (0.48 mL, 4.1 mmol) was added dropwise thereto. After 15 hours, formed solids were filtered and the filtrate was distilled under reduced pressure. Silica gel column-chromatography of the remaining residue was performed to give the title compound of white solid (0.28 g, 12%).

$^1$H NMR(CDCl$_3$): 7.91 (dd,2H), 7.48 (m,4H), 7.29-7.04 (m,7H), 4.13 (t,2H), 3.92 (m,2H), 3.57 (s,2H), 3.13 (t,2H), 3.04 (t,2H), 2.51 (m,4H), 2.30 (m,2H), 2.00 (m,2H), 1.78 (m,2H), 1.63 (m,2H);

EXAMPLE 10

Hydrochloric acid salt of N-[3-(2,4-dioxo-1,4-dihydro-2H-quinazolin-3-yl)propyl]-N-{4-[3-(2,4-dioxo-1,4-dihydro-2H-quinazolin-3-yl)propylamino] butyl}benzamide (Compound 10)

In the above Example 5, benzoyl chloride (0.69 g, 4.9 mmol) was used instead of ethyl chloroformate. The same procedure described in the above Example 5 was performed to give the title compound of white solid (0.2 g, 7.8%).

$^1$H NMR (DMSO-$d_6$): 7.94-7.84 (m,2H), 7.65 (m,2H), 7.38 (m,2H), 7.22-7.01 (m,7H), 3.96-3.72 (m,4H), 3.48-3.16 (m,4H), 2.89-2.64 (m,4H), 1.96-1.82 (m,4H), 1.62-1.34 (m,4H);

EXAMPLE 11

[3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid tert-butyl ester (Compound 11)

3-(3-{4-[3-(2,4-dioxo-1,4-dihydro-2H-quinazolin-3-yl) propylamino]butylamino}propyl)-1H-quinazoline-2,4-dione (2 g, 4.1 mmol) was dissolved in pyridine 20 ml and then cooled. 0.93 g di-tert-butyl dicarbonate (4.3 mmol) was added thereto. After 3 hours, pyridine was removed under reduced pressure, and silica gel column chromatography was performed to give the title compound of yellow solid (0.25 g, 10.4%).

$^1$H NMR (MeOD): 7.99 (m,2H), 7.60 (m,2H), 7.22-7.09 (m,4H), 4.04 (m,4H), 3.25 (t,4H), 2.59 (m,4H), 1.90 (m,4H), 1.60-1.48 (m,4H), 1.40 (s,9H);

EXAMPLE 12

Hydrochloric acid salt of N-[3-(2,4-dioxo-1,4-dihydro-2H-quinazolin-3-yl)propyl]-N-{4-[3-(2,4-dioxo-1,4-dihydro-2H-quinazolin-3-yl)propylamino] butyl}methansulfonamide (Compound 12)

3-(3-{4-[3-(2,4-dioxo-1,4-dihydro-2H-quinazolin-3-yl) propylamino]butylamino}propyl)-1H-quinazoline-2,4-dione (2 g, 4 mmol) was dissolved in hexamethylphosphoramide 10 mL with heating. Dichloromethane 30 mL was added thereto and cooled, and then methansulfonyl chloride (0.5 g, 4.3 mmol) was added thereto. After 2 hours, dichloromethane was removed under reduced pressure and silica gel column-chromatography of the remaining residue was performed to give the title compound of white solid (0.67 g, 27%).

$^1$H NMR (DMSO-$d_6$): 7.93 (m,2H), 7.64 (m,2H), 7.20 (m,4H), 3.97 (t,2H), 3.91 (t,2H), 3.17 (m,4H), 2.90 (s,3H), 2.89 (m,4H), 1.97 (m,2H), 1.85 (m,2H), 1.61 (s,4H);

EXAMPLE 13

N-(4-{benzyl-[3-(2,4-dioxo-1,4-dihydro-2H-quinazolin-3-yl)propyl]amino}butyl)-N-[3-(2,4-dioxo-1,4-dihydro-2H-quinazolin-3-yl)propyl]acetamide (Compound 13)

3-3-[4-({N-[3-(2,4-dioxo-1,4-dihydro-2,1-quinazolin-3-yl)propyl]benzyl}amino)butylamino]propyl-1H-quinazoline-2,4-dione (0.28 g, 0.48 mmol) was dissolved in 5 mL dichloromethane. Triethylamine (0.13 mL, 0.96 mmol) and acetic anhydride (0.06 mL, 0.58 mmol) were added thereto and stirred for 1 hour. The organic layer was separated by addition of water and dried with magnesium sulfate. After filtration and concentration, silica gel column-chromatography of the remaining residue was performed to give the title compound of oil form (0.12 g, 40%).

$^1$H NMR (MeOD): 7.96 (t,2H), 7.58 (m,2H), 7.32 (d,2H), 7.25-7.06 (m,7H), 4.01 (m,4H), 3.64, 3.59 (s,2H), 3.41 (m,2H), 3.29 (m,2H), 2.54 (m,4H), 2.09, 2.04 (s,3H), 1.98-1.85 (m,4H), 1.63-1.49 (m,4H);

EXAMPLE 14

(4-{acetyl-[3-(2,4-dioxo-1,4-dihydro-2H-quinazolin-3-yl)propyl]amino}butyl)-[3-(2,4-dioxo-1,4-dihydro-2H-quinazolin-3-yl)propyl]carbamic acid ethyl ester (Compound 14)

In the above Example 4, hydrochloric acid salt of N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}acetamide 3 g (5.3 mmol) and ethyl chloroformate 0.6 mL (6.3 mmol) were used, instead of 3-(3-4-[3-(2,4-dioxo-1,4-dihydro-2H-quinazolin-3-yl)propylamino]butylaminopropyl)-1H-quinazoline-2,4-dione and acetic anhydride. The same procedure of the above Example 4 was performed to give the title compound of white solid (1.1 g, 34%) in the mix-solvent of pyridine and dichloromethane.

$^1$H NMR (CDCl$_3$); 10.40 (d,2H), 8.06 (m,2H), 7.56 (m,2H), 7.17 (m,4H), 4.10 (m,6H), 3.50-3.30 (m,8H), 2.10 (s,3H), 1.97 (m,4H), 1.55 (d,4H), 1.21 (m,3H);

EXAMPLE 15

3-[3-(4-{N-[3-(2,4-dioxo-1,4-dihydro-2H-quinazolin-3-yl)propyl]-N-benzylamino}butyl)-N-benzylamino]propyl-1H-quinazoline-2,4-dione (Compound 15)

In the above Example 9, the title compound (0.4 g, 15%) was obtained by filtering white solids formed by reaction of 15 hours.

$^1$H NMR (DMSO-d$_6$): 7.88 (d,2H), 7.61 (t,2H), 7.27-7.13 (m,14H), 3.88 (t,4H), 3.46 (s,4H), 2.39 (t,4H), 2.29 (s,4H), 1.72 (m,4H); 1.36 (s,4H);

EXAMPLE 16

[3-(2,4-dioxo-1,4-dihydro-2H-quinazolin-3-yl)propyl]-(4-{[3-(2,4-dioxo-1,4-dihydro-2H-quinazolin-3-yl)propyl]ethoxycarbonylamino}butyl)carbamic acid ethyl ester (Compound 16)

3-(3-{4-[3-(2,4-dioxo-1,4-dihydro-2H-quinazolin-3-yl)propylamino]butylamino}propyl)-1H-quinazoline-2,4-dione (2 g, 4.1 mmol) was dissolved in 40 mL pyridine and ethyl chloroformate (0.46 mL, 4.9 mmol) was added thereto. After 2 hours, pyridine was removed under reduced pressure and dichloromethane and water was added to the remaining residue. After each layer was separated, dichloromethane was removed and silica gel column-chromatography of the remaining residue was performed to give the title compound of yellow solid (0.61 g, 24%).

$^1$H NMR (CDCl$_3$): 8.09 (d,2H), 7.58 (t,2H), 7.20 (t,2H), 7.12 (d,2H), 4.09 (m,8H), 3.35-3.25 (m,8H), 1.96 (m,4H), 1.52 (s,4H), 1.21 (t,6H);

EXAMPLE 17

(4-{tert-butoxycarbonyl-[3-(2,4-dioxo-1,4-dihydro-2H-quinazolin-3-yl)propyl]amino}butyl)-[3-(2,4-dioxo-1,4-dihydro-2H-quinazolin-3-yl)propyl]carbamic acid tert-butyl ester (Compound 17)

In the above Example 11, the title compound of white solid (0.3 g, 11%) was obtained by taking another fraction of silica gel column-chromatography.

$^1$H NMR (CDCl$_3$): 10.08 (bs,2H), 8.09 (d,2H), 7.56 (t,2H), 7.19 (t,2H), 7.12 (d,2H), 4.05 (m,4H), 3.30-3.20 (m,8H), 1.94 (t,4H), 1.51 (s,4H), 1.42 (s,18H);

EXAMPLE 18

N-[3-(2,4-dioxo-1,4-dihydro-2H-quinazolin-3-yl)propyl]-N-(4-{[3-(2,4-dioxo-1,4-dihydro-2H-quinazolin-3-yl)propyl]methansulfonylamino}butyl)methansulfonamide (Compound 18)

In the above Example 12, the title compound of white solid (0.24 g, 9.1%) was obtained by taking another fraction of silica gel column-chromatography.

$^1$H NMR (DMSO-d$_6$): 11.36 (s,2H), 7.90 (d,2H), 7.62 (t,2H), 7.16 (m,4H), 3.90 (t,4H), 3.21-3.13 (m,8H), 2.88 (s,6H), 1.84 (m,4H), 1.56 (s,4H);

EXAMPLE 19

N-[3-(acetyl-{4-[3-(2,4-dioxo-1,4-dihydro-2H-quinazolin-3-yl)propylamino]butyl}amino)propyl]-4-hydroxybenzamide (Compound 19)

N-(3-{4-[3 (2,4-dioxo-1,4-dihydro-2H-quinazolin-3-yl)propylamino]butylamino}propyl)-4-hydroxybenzamide (1.27 g, 2.72 mmol) was dissolved in 10 mL pyridine and acetic anhydride (0.4 mL, 4.07 mmol) was added thereto. After 2 hours, pyridine was removed by distillation under reduced pressure and dichloromethane and water were added thereto. The organic layer was separated and removed. After concentration under reduced pressure, the remaining residue was treated by silica gel column-chromatography and ion exchange resin to give the title compound of oil form (0.06 g, 4.3%).

$^1$H NMR (MeOD): 8.00 (d,1H), 7.70 (d,2H), 7.63 (t,1H), 7.21 (d,1H), 6.80 (d,2H), 4.09 (t,2H), 3.39 (m,6H), 2.77 (m,4H), 2.12, 2.09 (s,3H), 1.99-1.82 (m,4H), 1.59 (m,4H);

EXAMPLE 20

N-[3-(4-{acetyl-[3-(2,4-dioxo-1,4-dihydro-2H-quinazolin-3-yl)propyl]amino}butylamino)propyl]-4-hydroxybenzamide (Compound 20)

In the above Example 19, the title compound of oil form (0.06 g, 4.0%) was obtained by taking another fraction of silica gel column-chromatography and treating the fraction with CG-50 ion exchange resin.

$^1$H NMR (MeOD): 7.99 (m,1H), 7.70 (d,2H), 7.61 (m,1H), 7.17 (m,2H), 6.80 (d,2H), 4.01 (m,2H), 3.42 (m,6H), 2.87 (m,4H), 2.10 (s,3H), 1.97-1.90 (m,4H), 1.64 (m,4H);

EXAMPLE 21

N-{3-[acetyl-(4-{acetyl-[3-(2,4-dioxo-1,4-dihydro-2H-quinazolin-3-yl)propyl]amino}butyl)amino]propyl}-4-hydroxybenzamide (Compound 21)

In the above Example 19, the title compound of white solid (0.53 g, 35.4%) was obtained by taking another fraction of silica gel column-chromatography.

$^1$H NMR (MeOD): 7.98 (t,1H), 7.70 (dd,2H), 7.60 (m,1H), 7.15 (m,2H), 6.80 (dd,2H), 3.99 (m,2H), 3.42-3.30 (m,10H), 2.09 (t,3H), 2.07 (t,3H), 1.92-1.78 (m,4H), 1.55 (m, 4H);

EXAMPLE 22

N-[4-(2,4-dioxo-1,4-dihydro-2H-quinazolin-3-yl)butyl]-N-[3-(2,4-dioxo-1,4-dihydro-2H-quinazolin-3-yl)propyl]acetamide (Compound 22)

In the above Example 4, 3-{4-[3-(2,4-dioxo-1,4-dihydro-2H-quinazolin-3-yl)propylamino]butyl}-1H-quinazoline-2,4-dione (1 g, 2.3 mmol) was used instead of 3-(3-4-[3-(2,4-dioxo-1,4-dihydro-2H-quinazolin-3-yl)propylamino]butylaminopropyl)-1H-quinazoline-2,4-dione. The same procedure of the above Example 4 was performed to give the title compound of white solid (0.89 g, 81%) in the mix-solvent of pyridine and dichloromethane.

$^1$H NMR (MeOD): 7.98 (m,2H), 7.60 (m,2H), 7.16 (m,4H), 4.02 (m,4H), 3.42 (m,2H), 2.09 (d,3H), 1.95 (m,2H), 1.64 (m,4H);

EXAMPLE 23

3-(2-{3-[2-(2,4-dioxo-1,4-dihydro-2H-quinazolin-3-yl)ethylamino]propylamino}ethyl)-1H-quinazoline-2,4-dione (Compound 23)

In the above Example 7, N,N'-bis(2-aminoethyl)-1,3-propanediamine 2.4 g (14.8 mmol) was used instead of N-(3-aminopropyl)butane-1,4-diamine. The same procedure of the above Example 7 was performed to give the title compound of yellow solid (3.7 g, 55%).

$^1$H NMR (DMSO-d$_6$): 7.88 (d,2H), 7.59 (t,2H), 7.14 (m,4H), 3.92 (t,4H), 2.65 (t,4H), 2.47 (m,4H), 1.43 (m,2H);

EXAMPLE 24

3-(3-{3-[3-(2,4-dioxo-1,4-dihydro-2H-quinazolin-3-yl)propylamino]propylamino}propyl)-1H-quinazoline-2,4-dione (Compound 24)

In the above Example 7, N,N'-bis(3-aminopropyl)-1,3-propanediamine 2.8 g (14.8 mmol) was used instead of N-(3-aminopropyl)butane-1,4-diamine. The same procedure of the above Example 7 was performed to give the title compound of white solid (2.9 g, 41%).

$^1$H NMR (DMSO-d$_6$): 7.91 (d,2H), 7.63 (t,2H), 7.17 (m,4H), 3.92 (t,4H), 2.49 (t,8H), 1.70 (m,4H), 0.49 (m,2H);

EXAMPLE 25

3-(3-{4-[3-(2,4-dioxo-1,4-dihydro-2H-quinazolin-3-yl)propylamino]-2-butenylamino}propyl)-1H-quinazoline-2,4-dione (Compound 25)

In the above Example 7, N,N'-bis(3-aminopropyl)-2-butene-1,4-diamine 2.96 g (14.8 mmol) was used instead of N-(3-aminopropyl)butane-1,4-diamine. The same procedure of the above Example 7 was performed to give the title compound of white solid (4.5 g, 62%).

$^1$H NMR (DMSO-d$_6$): 7.91 (d,2H), 7.62 (t,2H), 7.17 (m,4H), 5.51 (s,2H), 3.91 (t,4H), 3.06 (s,4H), 2.47 (m,4H), 1.68 (m,4H);

EXAMPLE 26

(4-{tert-butoxycarbonyl-[3-(1-methyl-2,4-dioxo-1,4-dihydro-2H-quinazolin-3-yl)propyl]amino}butyl)-[3-(1-methyl-2,4-dioxo-1,4-dihydro-2H-quinazolin-3-yl)propyl]carbamic acid tert-butyl ester (Compound 26)

(4-{tert-butoxycarbonyl-[3-(2,4-dioxo-1,4-dihydro-2H-quinazolin-3-yl)propyl]amino}butyl)-[3-(2,4-dioxo-1,4-dihydro-2H-quinazolin-3-yl)propyl]carbamic acid tert-butyl ester (2 g, 2.9 mmol) was dissolved in 10 mL tetrahydrofuran and 10 mL dichloromethane and cooled. Sodium hydride (0.2 g, 8.3 mmol) and methyl iodide (0.6 mL, 9.6 mmol) were added thereto and stirred for 2 hours. After the solvent was concentrated under reduced pressure, silica gel column-chromatography of the remaining residue was performed to give the title compound of oil form (1.9 g, 91%).

$^1$H NMR (CDCl$_3$): 8.21 (d,2H), 7.66 (t,2H), 7.24 (t,2H), 7.18 (d,2H), 4.09 (t,4H), 3.59 (s,6H); 3.26-3.19 (m,8H), 1.91 (m,4H), 1.48 (s,4H), 1.40 (s,18H);

EXAMPLE 27

Dihydrochloric acid salt of 1-methyl-3 (3-{4-[3-(1-methyl-2,4-dioxo-1,4-dihydro-2H-quinazolin-3-yl)propylamino]butylamino}propyl)-1H-quinazoline-2,4-dione (Compound 27)

(4-{tert-butoxycarbonyl-[3-(1-methyl-2,4-dioxo-1,4-dihydro-2H-quinazolin-3-yl)propyl]amino}butyl)-[3-(1-methyl-2,4-dioxo-1,4-dihydro-2H-quinazolin-3-yl)propyl]carbamic acid tert-butyl ester (1.8 g, 2.5 mmol) was dissolved in 20 mL methanol, concentrated hydrochloric acid was added thereto and stirred. After methanol was concentrated, the title compound of white solid (1.3 g, 88%) was obtained by crystallization.

$^1$H NMR (D$_2$O): 7.81 (d,2H), 7.71 (t,2H), 7.25 (t,2H), 7.19 (d,2H), 4.04 (t,4H), 3.34 (s,6H), 3.13 (m,8H), 2.10 (m,4H), 1.89 (s,4H);

EXAMPLE 28

Dihydrochloric acid salt of 3-(3-{4-[3-(1,3-dioxo-1,3-dihydro-isoindole-2-yl)propylamino]butylamino}propyl)-1H-quinazoline-2,4-dione (Compound 28)

3-{3-[4-(3-aminopropylamino)butylamino]propyl}-1H-quinazoline-2,4-dione (1.06 g, 3.1 mmol) and diethyl phthalate (0.68 g, 3.1 mmol) was heated and stirred at 125~130° C. After 3 hours, 25 mL isopropylalcohol and concentrated hydrochloric acid were added thereto for forming a solid. Silica gel column-chromatography of the solid obtained by filtration was performed to give the title compound of white solid (0.25 g, 15%).

$^1$H NMR (D$_2$O): 7.77 (d,1H), 7.71 (m,4H), 7.61 (m,1H), 7.19 (t,1H), 6.99 (d,1H), 3.98 (t,2H), 3.71 (t,2H), 1.10 (m,8H), 2.06 (m,4H), 1.81 (s,4H);

EXAMPLE 29

Dihydrochloric acid salt of 3-(3-{2-[3-(2,4-dioxo-1, 4-dihydro-2H-quinazolin-3-yl)propylamino] ethylamino}propyl)-1H-quinazoline-2,4-dione (Compound 29)

In the above Example 7, N,N'-bis(3-aminopropyl)ethyl-enediamine (2.5 g, 14.3 mmol) was used instead of N-(3-aminopropyl)butane-1,4-diamine. The same procedure of above Example 7 was performed to form a solid and concentrated hydrochloric acid was then treated to give the title compound of white solid (1.5 g, 9.5%) in methanol.

$^1$H NMR (D$_2$O): 7.91 (d,2H), 7.64 (m,2H), 7.25 (m,2H), 7.07 (d,2H), 4.07 (t,4H), 3.48 (s,4H), 3.21 (t,4H), 2.12 (m,4H);

EXAMPLE 30

[3-(2,4-dioxo-1,4-dihydro-2H-quinazolin-3-yl)pro-pyl]-(4-{[3-(2,4-dioxo-1,4-dihydro-2H-quinazolin-3-yl)propyl]hexylamino}butyl)carbamic acid tert-butyl ester (Compound 30)

[3-(2,4-dioxo-1,4-dihydro-2H-quinazolin-3-yl)propyl]-{4-[3-(2,4-dioxo-1,4-dihydro-2H-quinazolin-3-yl)propy-lamino]butyl}carbamic acid tert-butyl ester (2 g, 3.4 mmol) was dissolved in 40 mL tetrahydrofuran. Sodium hydride (0.16 g, 6.7 mmol) and 1-bromohexane (0.67 g, 4.0 mmol) were added thereto and stirred under reflux. The solvent was concentrated under reduced pressure, and silica gel column-chromatography of the remaining residue was performed to give the title compound of white solid (0.52 g, 23%).

$^1$H NMR (MeOD): 7.99 (m,2H), 7.61 (m,2H), 7.20 (m,2H), 7.12 (dd,2H), 4.04 (m,4H), 3.26 (m,4H), 2.74 (m,6H), 193 (m,4H), 1.54 (m,6H), 1.40 (s,9H), 1.29 (s,6H), 0.88 (t,3H);

EXAMPLE 31

Dihydrochloric acid salt of 3-[3-(4-{N-[3-(2,4-di-oxo-1,4-dihydro-2H-quinazolin-3-yl)propyl]-N-hexylamino}butylamino)propyl]-1H-quinazoline-2, 4-dione (Compound 31)

[3-(2,4-dioxo-1,4-dihydro-2H-quinazolin-3-yl)propyl]-(4-{[3-(2,4-dioxo-1,4-dihydro-2H-quinazolin-3-yl)propyl] hexylamino}butyl)carbamic acid tert-butyl ester 0.4 g (0.6 mmol) was deprotected by the same procedure of the above Example 27 and separated by chromatography to give the title compound of white solid (0.1 g, 26%).

$^1$H NMR (MeOD): 7.97 (m,2H), 7.60 (m,2H), 7.20 (m,2H), 7.11 (t,2H), 4.13 (t,2H), 4.04 (t,2H), 3.04 (m,4H), 175 (t,2H), 2.67 (m,4H), 2.10 (m,2H), 1.91 (m,2H), 1.79 (t,2H), 1.70 (m,2H), 1.55 (m,2H), 1.30 (m,6H), 0.88 (t,3H);

EXAMPLE 32

(4-{tert-butoxycarbonyl-[3-(1-hexyl-2,4-dioxo-1,4-dihydro-2H-quinazolin-3-yl)propyl]amino}butyl)-[3-(1-hexyl-2,4-dioxo-1,4-dihydro-2H-quinazolin-3-yl) propyl]carbamic acid tert-butyl ester (Compound 32)

(4-{tert-butoxycarbonyl-[3-(2,4-dioxo-1,4-dihydro-2H-quinazolin-3-yl)propyl]amino}butyl)-[3-(2,4-dioxo-1,4-di-hydro-2H-quinazolin-3-yl)propyl]carbamic acid tert-butyl ester (3 g, 4.3 mmol) was dissolved in 120 mL acetonitrile. Potassium carbonate (3.45 g, 25.0 mmol) and 1-bromohexane (3.5 g, 21.1 mmol) were added thereto and stirred for 3 hours under reflux. The solvent was concentrated under reduced pressure, and silica gel column-chromatography of the remaining residue was performed to give the title compound of colorless oil form (3.7 g, 99%).

$^1$H NMR (CDCl$_3$): 8.13 (d,2H), 7.57 (t,2H), 7.14 (t,2H), 7.09 (d,2H), 4.01 (m,8H), 3.13 (m,8H), 1.84 (m,4H), 1.64 (m,4H), 1.36 (s,18H), 1.41-1.25 (m,16H), 0.82 (t,6H);

EXAMPLE 33

Dihydrochloric acid salt of 1-hexyl-3-(3-{4-[3-(1-hexyl-2,4-dioxo-1,4-dihydro-2H-quinazolin-3-yl) propylamino]butylamino}propyl)-1H-quinazoline-2, 4-dione (Compound 33)

(4-{tert-butoxycarbonyl-[3-(1-hexyl-2,4-dioxo-1,4-dihy-dro-2H-quinazolin-3-yl)propyl]amino}butyl)-[3-(1-hexyl-2, 4-dioxa-1,4-dihydro-2H-quinazolin-3-yl)propyl]carbamic acid tert-butyl ester (2 g, 2.3 mmol) was de-protected by the same procedure as the above Example 27 and crystallized in ethanol to give the title compound of white solid (1.07 g, 63%).

$^1$H NMR (MeOD): 8.15 (d,2H), 7.78 (m,2H), 7.43 (d,2H), 7.30 (t,2H), 4.17 (m,8H), 3.09 (t,8H), 2.12 (m,4H), 1.84 (s,4H), 1.72 (m,4H), 1.45-1.35 (m,12H), 0.91 (t,6H);

EXAMPLE 34

[3-(2,4-dioxo-1,4-dihydro-2H-quinazolin-3-yl)pro-pyl]-(4-{[3-(2,4-dioxo-1,4-dihydro-2H-quinazolin-3-yl)propyl]heptanoylamino}butyl)carbamic acid tert-butyl ester (Compound 34)

[3-(2,4-dioxo-1,4-dihydro-2H-quinazolin-3-yl)propyl]-{4-[3-(2,4-dioxo-1,4-dihydro-2H-quinazolin-3-yl)propy-lamino]butyl}carbamic acid tert-butyl ester (0.4 g, 0.7 mmol) was reacted with hepatanoic anhydride (0.2 g, 0.8 mmol) instead of acetic anhydride of above Example 4. The title compound of white solid (0.37 g, 88%) was obtained by the same procedure as the above Example 4.

$^1$H NMR (CDCl$_3$): 8.10 (m,2H), 7.58 (m,2H), 7.26-7.10 (m,4H), 4.08 (m,4H), 3.49-3.23 (m,8H), 2.28 (t,2H), 1.95 (m,4H), 1.66-1.50 (m,6H), 1.43 (d,9H), 1.27 (m,6H), 0.87 (m,3H);

EXAMPLE 35

Hydrochloric acid salt of [3-(2,4-dioxo-1,4-dihydro-2H-quinazolin-3-yl)propyl]-{4-[3-(2,4-dioxo-1,4-dihydro-2H-quinazolin-3-yl)propylamino] butyl}heptanoic amide (Compound 35)

Using [3-(2,4-dioxo-1,4-dihydro-2H-quinazolin-3-yl)pro-pyl]-(4-{[3-(2,4-dioxo-1,4-dihydro-2H-quinazolin-3-yl) propyl]heptanoylamino}butyl)carbamic acid tert-butyl ester (0.36 g, 0.5 mmol), the title compound of white solid (0.2 g, 61%) was obtained by the same procedure as the above Example 31.

¹H NMR (MeOD): 8.01 (m,2H), 7.63 (m,2H), 7.23-7.13 (m,4H), 4.14 (t,2H), 4.05 (m,2H), 3.45 (m,4H), 3.02 (m,4H), 2.35 (m,2H), 2.10-1.95 (m,4H), 1.76-1.55 (m,6H), 1.27 (m,6H), 0.87 (m,3H);

EXAMPLE 36

Hydrochloric acid salt of N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-2,2,2-trifluoroacetamide (Compound 36)

In the above Example 3, trifluoroacetic anhydride 1.5 g (7.3 mmol) was used instead of acetic anhydride, and the title compound of yellow solid (0.6 g, 15.8%) was obtained by the same procedure as the above Example 3.
¹H NMR (MeOD): 8.00 (m,2H), 7.63 (m,2H), 7.25-7.13 (m,4H), 4.14 (m,2H), 4.06 (m,2H), 3.54 (m,4H), 3.01 (m,4H), 2.07 (m,4H), 1.74 (m,4H);

EXAMPLE 37

N-[3-(2,4-dioxo-1,4-dihydro-2H-quinazolin-3-yl)propyl]-N-{4-[[3-(2,4-dioxo-1,4-dihydro-2H-quinazolin-3-yl)propyl]-(2,2,2-trifluoroacetyl)amino]butyl}-2,2,2-trifluoroacetamide (Compound 37)

The title compound of white solid (1.1 g, 26.4%) was obtained by taking another fraction of silica gel column-chromatography and solid formed in the above Example 36.
¹H NMR (MeOD): 8.01 (m,2H), 7.62 (m,2H), 7.23-7.12 (m,4H), 4.03 (m,4H), 3.50 (m,8H), 2.01 (m,4H), 1.65 (m,4H);

EXAMPLE 38

Hydrochloric acid salt of N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-2-methoxyacetamide (Compound 38)

Starting material of above Example 50.5 g (1.0 mmol) and methoxyacetyl chloride (0.12 g, 1.1 mmol) instead of ethyl chloroformate were used. The same procedure of the above Example 5 was performed to give the title compound of white solid (0.1 g, 16.4%).
¹H NMR (MeOD). 8.00 (m,2H), 7.63 (m,2H), 7.23-7.12 (m,4H), 4.14 (m,4H), 4.05 (m,2H), 3.48-3.32 (m,7H), 3.01 (m,4H), 2.12-2.01 (m,4H), 1.70 (m,4H);

EXAMPLE 39

Hydrochloric acid salt of [3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid benzyl ester (Compound 39)

Benzyl chloroformate 1.05 g (6.1 mmol) instead of acetic anhydride of the above Example 3 was used, and the same procedure of the above Example 3 was performed to give the title compound of yellow solid (0.34 g, 8.4%).
¹H NMR (MeOD): 8.00 (m,2H), 7.63 (m,2H), 7.33-7.19 (m,7H), 7.13 (t,2H), 5.08 (s,2H), 4.13 (t,2H), 4.00 (m,2H), 3.41 (m,4H), 3.00-2.92 (m,4H), 2.06 (m,2H), 1.96 (m,2H), 1.69 (bs,4H);

EXAMPLE 40

N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-4-methylbenzenesulfonamide (Compound 40)

Instead of methansulfonyl chloride of the above Example 12, p-toluenesulfonyl chloride 1.4 g (7.3 mmol) was used. The same procedure of above Example 12 was performed in methanol and then CG-50 ion exchange resin was treated to give the title compound of white solid (0.3 g, 8%).
¹H NMR (MeOD): 7.95 (d,2H), 7.66 (d,2H), 7.58 (m,2H), 7.33 (d,2H), 7.18-7.08 (m,4H), 4.02 (m,4H), 3.23 (t,2H), 3.15 (t,2H), 2.55 (q,4H), 2.39 (s,3H), 1.89 (m,4H), 1.63 (m,2H), 1.52 (m,2H);

EXAMPLE 41

N-[3-(2,4-dioxo-1,4-dihydro-2H-quinazolin-3-yl)propyl]-N-(4-{[3-(2,4-dioxo-1,4-dihydro-2H-quinazolin-3-yl)propyl]-4-methylbenzenesulfonylamino}butyl)-4-methylbenzenesulfonamide (Compound 41)

In the above Example 40, the title compound of white solid (1.27 g, 26%) was obtained by taking another fraction of silica gel column-chromatography.
¹H NMR (DMSO-$d_6$): 11.40 (s,2H), 7.90 (d,2H), 7.62 (m,6H), 7.32 (d,4H), 7.17 (m,4H), 3.86 (t,4H), 3.08 (m,8H), 2.35 (s,6H), 1.75 (m,4H), 1.42 (s,4H);

EXAMPLE 42

Dihydrochloric acid salt of 3-(3-{4-[3-(2,5-dioxo-pyrrolidine-1-yl)propylamino]butylamino}propyl)-1H-quinazoline-2,4-dione (Compound 42)

Starting material 1.5 g (4.3 mmol) of the above Example 28 was used, and succinic anhydride (0.43 g, 4.33 mmol) instead of diethyl phthalate was used. The same procedure of the above Example 28 was performed to give the title compound of yellow solid (0.23 g, 11%).
¹H NMR (MeOD): 8.05 (d,1H), 7.67 (m,1H), 7.25 (t,1H), 7.20 (d,1H), 4.16 (t,2H), 3.61 (t,2H), 3.07 (m,8H), 2.72 (s,4H), 2.12 (m,2H), 1.97 (m,2H), 1.82 (m,4H);

It will be explained in detail that the compound of the above formula (I) according to the present invention has excellent effects as a neuro-protecting agent, by the following Examples using the compounds prepared by the above Examples.

The following Experimental Examples are set forth to aid in the understanding of the invention, and should not be construed to limit in any way the invention set forth in the claims which follow thereafter.

EXPERIMENTAL EXAMPLE 1

Experiment of Anti-Stroke Effect in Middle Cerebral Artery Occlusion (MCAO) Model Male rats of SD species with 290-300 g of body weight were used as laboratory animals, and 8 rats were used in each experiment group. The operation was performed by using the method of Nagasawa et al. (Nagasawa, H. and Gogure, K. 1989, Stroke, 20: 1037-1043).

The rats were anesthetized by Ketamine, and the operation was performed as body temperature was maintained using thermoplate. The cerebral region was incised following the median line of the neck, and the left common carotid artery, internal carotid artery and external carotid artery were separated, taking care not to damage the vagus nerve. The common carotid artery and external carotid artery were ligatured, and a probe was inserted into the internal carotid artery from the branch point of the internal and external carotid arteries. And then the fundus of the middle cerebral artery was occluded by ligature just on the upper side of the insertion region. A probe was made by heating the end of a 4-0 nylon surgical suture (Dafilon, B. Braun, Germany) and cut into 30 mm. The 7-9 mm end of the probe was coated with the mixture of silicon (Xantopren VL plus, Heraeus Kulzer, Germany) and curing agent (Optosyl-Xantopren VL plus, Heraeus Kulzer, Germany), and the thickness was to be 0.3-0.4 mm. After the intervention of the probe insertion and the animals came out of the anesthetic, individuals in which neurological deficit symptom (right direction circling) was observed were included in the ischemia group.

After 3 hours of ischemia, the inserted probe was removed to reperfuse blood circulation. The brain was extracted after 24 hours, followed by histological staining.

Figure 1:
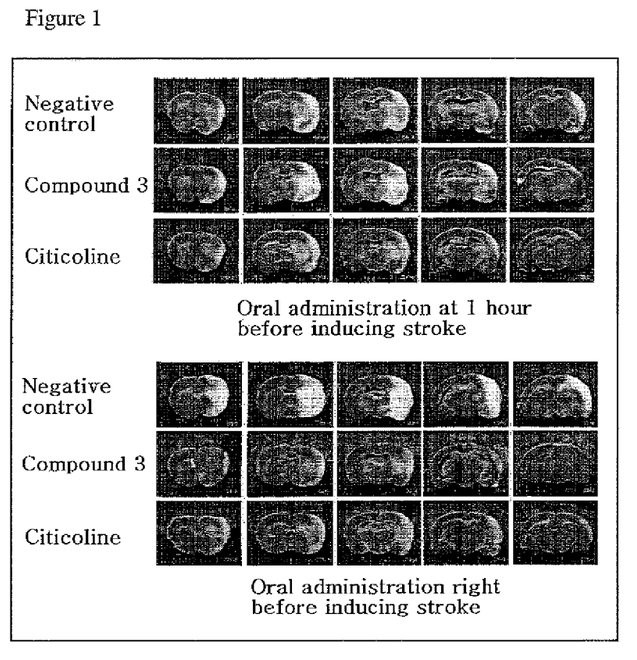
FIG. 1 shows the anti-stroke effect of compound 3 in a middle cerebral artery occlusion (MCAO) model. The red color (stained) represents the normal brain area and the white color (unstained) represents the occlusion area. 100 mg/kg of compound 3 and 2000 mg/kg of citicoline were administered at 1 hour and right before inducing stroke (eight mice were used in each experiment group).

The compound 3 was administered at a programmed time before or after insertion of the probe with oral or intravenous administration. TTC (2,3,5-triphenyltetrazolium chloride) staining was performed to estimate the damage of brain tissue by ischemia. Procephalon of the extracted brain was sliced into 2 mm of sequential slice by using brain matrix (ASI instrument, Warren, Mich., USA). The slices were put into 2% of TTC solution and incubated at 37° C. for 60 minutes for staining. The TTC stained brain slice was fixed in 10% of formalin buffer and the front of the each slice was photographed with a digital camera. The infarcted areas ($cm^2$) that were not stained with deep red in each acquired image were measured using an image analyzer, and total infarcted volume ($cm^3$) was calculated by multiplying the thickness of the slices As a result, the oral administration (100 mg/kg) of compound 3 showed the inhibitory effect that percentage of cerebral infarcted volume was 22.3% and 69.8% compared to negative control by oral administration done by an hour and right before inducing stroke. Citicoline (2 g/kg) administered as a positive control was observed 51.1 and 37.8% each (Table 1 and FIG. 1).

In the experiment, the probe was removed after stoke induction so that circulation was reperfused. Compound 3 was then administered in a split time with 5 mg/kg dose, the inhibitory effect of necrosis volume of 62.7% was observed even though administration was performed 12 hours after reperfusion. On the other hand, MK-801 administered as a positive control showed the maximum effect at 30 minutes after reperfusion (Table 2). Therefore, Compound 3 has obvious effects on prevention and treatment of stroke, and may also be applied to patients whose treatment was delayed after the onset of stroke.

TABLE 1

Anti-stroke effect by oral administration

| Treatment time (before inducing ischemic stroke) | Compound 3 (100 mg/kg, po) | | Citicoline (2 g/kg, po) | |
|---|---|---|---|---|
| | Infarcted volume ($cm^3$, Mean ± standard deviation) | Inhibitory percentage compared to negative control(%) | Infarcted volume ($cm^3$, Mean ± standard deviation) | Inhibitory percentage compared to negative control (%) |
| 0 | 0.14 ± 0.02 | 69.8 | 0.28 ± 0.04 | 37.8 |
| 1 | 0.35 ± 0.07 | 22.3 | 0.22 ± 0.03 | 51.1 |

* Infarcted volume of negative control 0.45 ± 0.03

TABLE 2

Anti-stroke effect by intravenous administration

| Treatment time (After reperfusion) | Compound 3 (5 mg/kg, iv) | | MK-801 (1 mg/kg, iv) | |
|---|---|---|---|---|
| | Infarcted volume ($cm^3$, Mean ± standard deviation) | Inhibitory percentage compared to negative control(%) | Infarcted volume ($cm^3$, Mean ± standard deviation) | Inhibitory percentage compared to negative control (%) |
| −0.5 | 0.14 ± 0.03 | 67.2 | 0.19 ± 0.06 | 55.4 |
| 0.5 | 0.12 ± 0.03 | 72.3 | 0.21 ± 0.04 | 50.2 |
| 1 | 0.20 ± 0.04 | 53.8 | 0.31 ± 0.02 | 27.0 |
| 2 | 0.22 ± 0.02 | 49.9 | 0.33 ± 0.02 | 22.8 |
| 4 | 0.22 ± 0.09 | 47.9 | 0.28 ± 0.08 | 34.4 |
| 6 | 0.17 ± 0.04 | 60.9 | 0.37 ± 0.06 | 13.3 |
| 12 | 0.16 ± 0.04 | 62.7 | 0.39 ± 0.06 | 8.7 |
| 18 | 0.37 ± 0.03 | 13.5 | 0.40 ± 0.08 | 7.4 |
| 24 | 0.36 ± 0.08 | 16.3 | 0.39 ± 0.05 | 8.8 |

* Infarcted volume of negative control 0.43 ± 0.02

EXPERIMENTAL EXAMPLE 2

Inhibitory Effect of Excitable Neurotoxicity in Mixed Culture of Nerve Cells-Glial Cells Isolation and culture of nerve cells were performed by Choi's method (Choi, D. W. 1985, Neurosci. Lett., 58: 293-297). That is, the cortex was isolated in fetus ICR mouse that was 14 days pregnant, and then single cells were obtained from the tissue using pipette. The cells were aliquoted into $2 \times 10^5$/well density in a 24-well plate (Falcon) in which glial cells of cerebral cortex had been cultured in an incubator maintained at 37° C. with 5% $CO_2$ for over 3 weeks. The culture medium was supplemented with MEM (minimum essential medium, Sigma), 2 mM glutamine, 21 mM glucose, 26.5 mM bicarbonate, 10% fetal bovine serum (FBS). In 3-5 days after aliquot, 10 μM Ara-C (cytosine arabinoside) was treated to suppress proliferation of neuroglia. And it was treated with 100 μM NMDA and 1 μg/mL or 2 μg/mL of each sample (compound) to induce the death of nerve cells due to excitable toxicity for 20 minutes, in 12-15 days after aliquot. Because of nerve cell death, lactate dehydrogenase (LDH) accumulated in proportion to the number of dead cells. In 24 hours after drug treatment, the amount of dehydrogenase (LDH) released to outside of cells was measured by using an LDA measurement kit (CytoTox 96, Promega). After the reaction was completed, the change of absorbance depending on the amount of LDH was measured by using a microplate spectrophotometer.

The inhibitory effect on cell death compared with negative control was shown in Table 3, and it showed a significant effect.

TABLE 3

Protecting effect on NMDA-induced nerve cell death in mixed culture of nerve cells-glial cells

| Compound | Inhibitory effect of cell death by NMDA-induced excitable neurotoxicity, % | | Compound | Inhibitory effect of cell death by NMDA-induced excitable neurotoxicity, % | |
|---|---|---|---|---|---|
| | 1 µg/ml | 2 µg/ml | | 1 µg/ml | 2 µg/ml |
| MK-801 | 49.0 | 63.6 | 21 | 19.6 | 16.6 |
| 1 | 16.1 | 2.4 | 22 | 17.0 | 14.0 |
| 2 | 11.0 | 0.7 | 23 | 36.0 | 32.2 |
| 3 | 45.5 | 54.4 | 24 | 27.4 | 30.3 |
| 4 | 22.3 | 7.4 | 25 | 35.2 | 28.8 |
| 5 | 11.4 | 39.4 | 26 | 8.8 | 29.7 |
| 7 | 26.0 | 39.7 | 27 | 33.7 | 36.0 |
| 8 | 20.0 | 28.2 | 28 | 23.1 | 22.4 |
| 9 | 21.4 | 33.3 | 29 | 8.5 | 29.5 |
| 10 | 15.4 | 13.7 | 30 | 38.3 | 44.4 |
| 11 | 15.0 | ND | 32 | 32.0 | 29.8 |
| 12 | 5.7 | 2.6 | 33 | 14.6 | 65.1 |
| 13 | 17.4 | 23.0 | 35 | 32.5 | 35.7 |
| 14 | 18.9 | 26.9 | 36 | 32.2 | 18.4 |
| 15 | 22.4 | 22.3 | 37 | 27.3 | 25.0 |
| 16 | 18.1 | ND | 38 | 33.5 | 13.5 |
| 17 | 21.0 | 10.7 | 39 | 30.8 | 17.1 |
| 18 | 44.4 | 21.0 | 40 | ND | 34.5 |
| 19 | 40.1 | 45.2 | 41 | ND | 28.5 |
| 20 | 36.4 | 42.5 | 42 | 24.6 | 21.8 |

ND: Not detected

EXPERIMENTAL EXAMPLE 3

Inhibitory Effect on $H_2O_2$-Mediated Cytotoxicity in SH-SY5Y Cells

SH-SY5Y cells that are oriented by nerve cell line from humans were cultured with $3 \times 10^4$ cell concentration in 96 well plate, and the sample was treated. After 30 minutes, 200 µM hydrogen peroxide was treated to induce toxicity for 24 hours. After the reaction was completed, the survival rate of cells was measured by MIT assay.

As a result, it was identified that the survival rate of SH-SY5Y cells was positively correlated with the concentration of Compound 4, and it showed about 35% of protecting effect on cells in the concentration of 100 µg/ml (Table 4).

TABLE 4

Inhibitory effect on oxidative toxicity induced by hydroperoxide

| concentration | inhibitory percentage (%) |
|---|---|
| 5 µg/ml | 2.0 ± 0.4 |
| 50 µg/ml | 18.1 ± 2.1 |
| 100 µg/ml | 34.5 ± 5.8 |

EXPERIMENTAL EXAMPLE 4

Inhibitory Effect on $ZnSO_4$-Mediated Cytotoxicity in SH-SY5Y Cells

SH-SY5Y cells were cultured with $3 \times 10^4$ cell concentration in 96 well plates, and the compound (50 µg/ml) was treated. After 30 minutes, 600 µM of zinc sulfate was treated to induce toxicity for 24 hours and survival rate of cells was measured by MTT assay. The result showed an inhibitory effect of 9.1 to 21.7% on toxicity (Table 5).

TABLE 5

Inhibitory effect on zinc-induced toxicity

| compound | inhibitory percentage (%) |
|---|---|
| 2 | 21.7 ± 4.1 |
| 3 | 17.6 ± 3.5 |
| 12 | 12.7 ± 4.3 |
| 35 | 9.1 ± 1.8 |

EXPERIMENTAL EXAMPLE 5

Inhibitory Effect on ROS Production in Brain Cells

Figure 2:
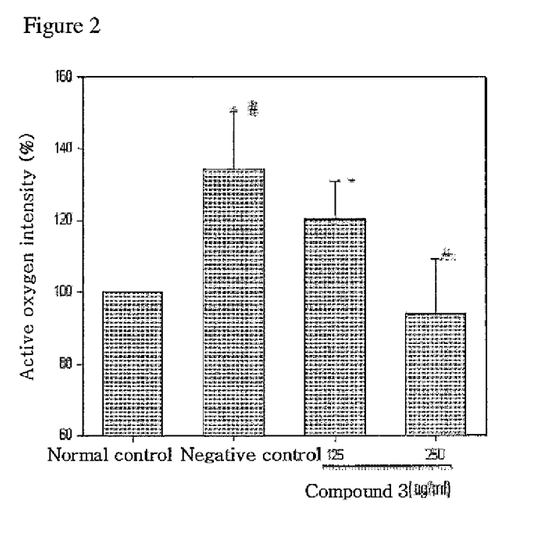
FIG. 2 shows an effect of compound 3 on the suppression of oxidative stress induced by NMDA of brain cells in mice. "Normal control" is normal cells without any treatment, and "negative control" is brain cells with treatment of 300 μM NMDA. 125 μg/mL and 250 μg/mL of compound 3 were administered (compounds-treated groups). Marks of #, * and ** are intended to show the significant difference of $P<0.05$, as compared with each corresponding control, in cases of carrying out ANOVA and Student-t test (#; to compare normal control with negative control; and * and **; to compare compounds-treated groups with negative control).

Oxidative stress was measured to test inhibitory effects on the production of reactive oxygen species (ROS) by using DCF-DA, which is a fluorescent probe. Brain cells were obtained from brain cortex of mouse to prepare cell solution with $2 \times 10^6$ cells/ml. Each brain cell was treated with 11 µM of DCF-DA followed by reaction in 37° C., 5% $CO_2$ incubator for an hour. After washing twice, Compound 3 was treated with a concentration of 125 µg/ml and 250 µg/ml. At the same time, 300 µM of NMDA was treated and it was incubated in 37° C., 5% $CO_2$ incubator for 24 hours. After the reaction was completed, fluorescence that showed reactive oxygen in reaction solution was measured by using fluorescence spectrophotometer (excitation 480 nm/emission, 535 nm). As a result, Compound 3 suppressed the oxidative stress induced by NMDA of nerve cells in a dose-dependent manner (FIG. 2).

ROS inhibitory effect of compounds was represented to the dose suppressing 50% of production of reactive oxygen compared to control. It was observed to increase of the activity of superoxide dismutase (SOD), an enzyme that plays a key role in the production of reactive oxygen, and a rate of increase was represented compared to control. The activity of superoxide dismutase (SOD) was measured by using a kit acquired in Sigma. As a result, most of the compounds showed lower doses of $ID_{50}$ compared to MK-801, which is positive control. It indicates that they have a superior effect with lower doses than MK-801.

TABLE 6

Inhibitory effect on ROS production in mouse brain cells

| compound | ROS inhibitory effect $ID_{50}$ (µg/ml) | compound | ROS inhibitory effect $ID_{50}$ (µg/ml) |
|---|---|---|---|
| MK-801 | 164.8 ± 17.6 | 27 | 21.9 ± 16.1 |
| 1 | 73.0 ± 14.1 | 28 | 30.9 ± 13.7 |
| 3 | 108.3 ± 27.2 | 29 | 10.1 ± 17.3 |
| 5 | 24.4 ± 10.5 | 30 | 79.5 ± 15.7 |
| 7 | 17.7 ± 17.3 | 32 | 14.4 ± 7.6 |
| 8 | 102.7 ± 20.4 | 33 | 172.7 ± 19.7 |
| 13 | 87.3 ± 10.9 | 35 | 140.0 ± 18.6 |
| 14 | 90.1 ± 12.2 | 37 | 22.9 ± 17.3 |
| 22 | 172.5 ± 23.6 | 38 | 136.1 ± 11.0 |
| 23 | 55.5 ± 27.2 | 39 | 32.3 ± 20.0 |
| 24 | 122.4 ± 32.4 | 40 | 31.0 ± 8.1 |
| 25 | 104.0 ± 32.5 | 41 | 27.2 ± 18.6 |
| | | 42 | 137.7 ± 21.0 |

TABLE 7

Effect on increase of superoxide dismutase (SOD) activity in mouse brain cells

| compound | Increase of SOD activity 100 μg/ml, compared to control | compound | Increase of SOD activity 100 μg/ml, compared to control |
|---|---|---|---|
| MK-801 | −0.5 ± 2.9 | 21 | −0.3 ± 3.7 |
| 1 | 0.7 ± 5.6 | 22 | 3.7 ± 0.8 |
| 2 | 2.8 ± 4.0 | 23 | 4.0 ± 10 |
| 3 | 3.2 ± 2.7 | 24 | 6.9 ± 3.8 |
| 4 | 0.6 ± 2.2 | 25 | 1.6 ± 9.3 |
| 5 | 2.5 ± 2.8 | 26 | 0.7 ± 5.7 |
| 7 | ND | 27 | 2.4 ± 7.8 |
| 8 | ND | 28 | ND |
| 9 | ND | 29 | 3.0 ± 1.1 |
| 10 | ND | 30 | 6.2 ± 6.2 |
| 11 | 2.3 ± 3.4 | 32 | 0.3 ± 7.1 |
| 12 | 2.8 ± 1.8 | 33 | ND |
| 13 | 7.6 ± 2.9 | 35 | 3.4 ± 7.9 |
| 14 | 2.7 ± 1.0 | 36 | 4.9 ± 1.2 |
| 15 | 1.3 ± 3.1 | 37 | 2.0 ± 5.8 |
| 16 | 7.5 ± 2.3 | 38 | 3.2 ± 4.9 |
| 17 | 0.3 ± 0.0 | 39 | 19.0 ± 6.3 |
| 18 | ND | 40 | 8.3 ± 3.2 |
| 19 | ND | 41 | 2.0 ± 0.9 |
| 20 | ND | 42 | 1.6 ± 2.6 |

Antagonistic effects of the compounds on NMDA receptor examined in Experimental Examples 2 to 5 demonstrated that the compounds of the present invention may be used as a drug not only to treat ischemic stroke but also to prevent and treat degenerative brain disease related to this receptor, such as epilepsy, amyotrophic lateral sclerosis (ALS), Parkinson's disease, Huntington's disease, Alzheimer's disease, and traumatic brain injury or spinal cord injury. It may also be used for memory improvement.

EXPERIMENTAL EXAMPLE 6

Experiment of Anti-Convulsant Effect

An experiment was performed by the method of Ali et al. (Ali, A. et al. 2006, Pharmacological Reports, 58: 242-245). A 10 mg/kg dose of compound was intraperitoneally administered to identify the anti-convulsant effect and the effect was observed (Table 8). Researching the process of activity was performed by the Anti-epileptic Drug Development Program (ADD) of NIH during development of the anti-convulsant drug. One of the assessed items of anti-convulsant activity in the first step of this program is the pentylentetrazole (PTZ) test. After administration of the testing drug, 80 mg/kg dose of PTZ was subcutaneously administered and it was observed for at least 30 minutes. After 10 mg/kg of the testing drug was administered, assessment was performed by estimating the initiation time of convulsion, duration until convulsion completely disappeared and mortality rate. It was assessed as having an anti-convulsant effect when a single episode of clonic spasm was not shown over 5 seconds on at least one of the 4 laboratory animals after PTZ administration.

TABLE 8

Anti-convulsant effect of compounds

| compound | Initiation time of convulsion (min) | Duration of convulsion (min) | Induction percentage of convulsion(%) | mortality rate(%) |
|---|---|---|---|---|
| negative control | 5.0 ± 0.7 | 46.7 ± 3.3 | 100(23/23) | 70(17/23) |
| positive control Diazepam | N.D.** | N.D.** | 0(0/6) | 0(0/6) |
| 1 | 16.1 ± 9.0* | 43.9 ± 9.0 | 83(5/6) | 67(4/6) |
| 2 | 12.9 ± 3.7** | 35.7 ± 7.1 | 100(6/6) | 67(4/6) |
| 3 | 34.7 ± 7.7** | 11.8 ± 5.6** | 50(6/12) | 17(2/12) |
| 7 | 3.1 + 0.3 | 42.9 ± 8.7 | 100(6/6) | 67(4/6) |
| 9 | 4.4 ± 0.7 | 39.8 ± 10.3 | 100(6/6) | 67(4/6) |
| 10 | 5.8 ± 1.4 | 49.9 ± 5.4 | 100(6/6) | 17(1/6) |
| 11 | 10.1 ± 4.9 | 44.9 ± 5.8 | 100(6/6) | 17(1/6) |
| 12 | 13.7 ± 6.2* | 39.3 ± 8.8 | 100(6/6) | 67(4/6) |
| 14 | 8.5 ± 1.8* | 2.9 ± 2.1** | 100(6/6) | 0(0/6) |
| 15 | 25.7 ± 7.2** | 34.3 ± 7.2 | 83(5/6) | 83(5/6) |
| 16 | 7.6 ± 1.7 | 6.4 ± 2.3** | 100(6/6) | 0(0/6) |
| 18 | 19.1 ± 8.4** | 5.2 ± 3.4** | 83(5/6) | 0(0/6) |
| 19 | 38.7 ± 1.5** | 1.8 ± 2.7** | 50(3/6) | 0(0/6) |
| 20 | 44.7 ± 11.0** | 0.9 ± 1.9** | 50(3/6) | 0(0/6) |
| 21 | 22.2 ± 11.9** | 6.7 ± 3.1** | 67(4/6) | 0(0/6) |
| 22 | 15.2 ± 9.0* | 7.0 ± 3.2** | 83(5/6) | 0(0/6) |
| 23 | 9.3 ± 2.5* | 28.7 ± 8.6* | 100(6/6) | 33(2/6) |
| 24 | 6.1 ± 1.7 | 35.7 ± 84 | 100(6/6) | 50(3/3) |
| 25 | 6.2 ± 1.5 | 48.3 ± 5.9 | 100(6/6) | 83(5/6) |
| 26 | 15.4 ± 9.0* | 33.0 ± 9.5 | 83(5/6) | 50(3/6) |
| 27 | 8.4 ± 2.6 | 35.8 ± 9.8 | 100(6/6) | 50(3/6) |
| 28 | 4.8 ± 2.2 | 26.9 ± 6.5* | 100(6/6) | 0(0/6) |
| 29 | 18.2 ± 9.1** | 30.3 ± 11.1 | 83(5/6) | 17(1/6) |
| 30 | 15.9 ± 9.0* | 44.1 ± 9.0 | 83(5/6) | 83(5/6) |
| 32 | 11.3 ± 4.5* | 29.8 ± 12.0 | 100(6/6) | 50(3/6) |
| 33 | 16.1 ± 2.2** | 36.6 ± 7.6 | 100(6/6) | 83(5/6) |
| 35 | 5.4 ± 1.6 | 33.3 ± 7.3 | 100(6/6) | 33(2/6) |
| 36 | 8.9 ± 2.3* | 25.1 ± 9.7* | 100(6/6) | 33(2/6) |
| 38 | 16.0 ± 9.0* | 11.2 ± 7.3** | 83(5/6) | 17(1/6) |
| 39 | 9.5 ± 2.8* | 19.8 ± 6.4** | 100(6/6) | 0(0/6) |
| 40 | 11.2 ± 2.4** | 42.3 ± 8.5 | 100(6/6) | 83(5/6) |
| 42 | 9.8 ± 4.1* | 18.2 ± 8.6** | 100(6/6) | 17(1/6) |

Each value represents mean value (n = 6) of measurement ( In the case of negative control, n = 23)
*Statistical significance compared with control (95% confidence)
**Statistical significance compared with control (99% confidence)
N.D. Not Detected

EXPERIMENTAL EXAMPLE 7

Relaxing Effect on Thoracic Aorta in Rats

After male rats of SD species (250-300 g) were anesthetized by inhalation of ether, their thoracic aortas were extracted and put into a Krebs buffer (mM; NaCl 118, NaHCO$_3$ 27.3, KCl 4.8, MgSO$_4$ 1.2, KH$_2$PO$_4$ 1.0, CaCl$_2$ 1.25, glucose 11.1). 2 mm of aortic ring was made under dissecting microscope and cultured in an organ bath to measure the tension of blood vessels. The organ bath was filled with Krebs buffer and saturated with 95% O$_2$, 5% CO$_2$ to maintain dissolved oxygen and physiological pH. Changing of tension was measured by a tension meter (Hugo-sachs, model K30) and recorded by physiological recorder (Coulbourn polygraph). The length of the blood vessels was increased step by step to make 1.0 g of basal tension for 90 minutes. The equilibrated blood vessel was contracted by phenylephrine (0.5 μM). When the contraction furrow reached equilibrium, compounds were added, followed by observation of relaxation response.

A result that Compound 3 was added with the dose of 50 μg/mL, 100 μg/mL and 200 μg/mL was listed in Table 9, and Compound 3 dose-dependently relaxed the thoracic aorta of rats contracted by phenylephrine (Table 9). The result that each compound was administered with a dose of 67 μg/mL was listed in Table 10, and this result may be presumed to delay cell death and induce the revival of death cells, owing to the increase of the bloodstream by the expansion of a blood vessel in a body.

TABLE 9

Dose-dependent relaxing effect on muscles of blood vessels

| | Dose (μg/mL) | Relaxation percentage (%), (Mean ± standard deviation) |
|---|---|---|
| Control | — | 0 |
| Compound 3 | 50 | 16.2 ± 4.4 |
| | 100 | 44.2 ± 8.5 |
| | 200 | 65.6 ± 7.1 |

Each value represents mean value ± standard deviation ( n = 3) of measurement.

TABLE 10

Relaxing effect on compounds on muscles of the blood vessel of thoracic aorta

| Compound | Relaxation percentage (%) | Compound | Relaxation percentage (%) |
|---|---|---|---|
| ME-801 | ND | 21 | 2.6 |
| 1 | 12.8 | 22 | ND |
| 2 | 10.9 | 23 | 20.4 |
| 3 | 27.4 | 24 | ND |
| 4 | 7.7 | 25 | 20.0 |
| 5 | 19.2 | 26 | 3.7 |
| 7 | 56.8 | 27 | ND |
| 8 | 35.7 | 28 | 8.3 |
| 9 | 95.5 | 29 | ND |
| 10 | 4.9 | 30 | 40.4 |
| 11 | 10.9 | 32 | ND |
| 12 | 10.9 | 33 | 38.5 |
| 13 | 9.3 | 35 | 42.6 |
| 14 | ND | 36 | ND |
| 15 | ND | 37 | 7.9 |
| 16 | ND | 38 | 88.2 |
| 17 | 51.7 | 39 | 54.8 |
| 18 | 42.4 | 40 | ND |
| 19 | 11.8 | 41 | 7.1 |
| 20 | 15.2 | 42 | 14.6 |

Each value represents mean (n = 3) of measurement.
ND: Not Detected

A superior relaxing effect of muscles of the blood vessel was observed, compared with control in most compounds.

[Industrial Applicability]

As mentioned above in the examples, the compounds of the present invention show an anti-stroke effect, antagonistic effect on NMDA receptor, inhibitory effect on $H_2O_2$ toxicity and $ZnSO_4$ toxicity in nerve cells, antioxidant effect in nerve cells, anti-convulsant effect and relaxing effect of thoracic aorta. Therefore, they can be used as a drug to prevent and treat aforementioned various diseases such as stroke, nerve system functional disorder, memory loss, cerebrovascular dysfunction, damage of brain and spinal cord, cerebral ischemia, dementia, Alzheimer's disease, Parkinson's disease and epilepsy.

The invention claimed is:

1. A method of treating a brain or nerve disorder selected from the group consisting of cerebral ischemia, ischemic stroke, hemorrhagic stroke, Alzheimer's disease, and epilepsy, comprising administering to a patient in need thereof a therapeutically effective amount of a compound of formula (I):

wherein
$R_1$ is hydrogen or alkyl;
each of $R_2$ and $R_3$ is independently selected from hydrogen, alkyl, $-COR_6$, $-SO_2R_7$, or substituted or unsubstituted phenyl or benzyl, wherein $R_6$ is alkyl, alkoxy, phenyl, phenyloxy or benzyloxy, each of which is unsubstituted or substituted with halogen, hydroxy, methoxy, ethoxy or nitro, and $R_7$ is unsubstituted or substituted lower alkyl or aryl;
A is $-(CH_2)_n$- or $-CH_2CH=CHCH_2-$, wherein n is an integer selected from 2 to 4;
$R_4$ is hydrogen and $R_5$ is hydrogen or benzoyl unsubstituted or substituted with one or more of halogen, hydroxy, alkoxy or nitro in benzene ring or when $R_4$ and $R_5$ together with N form a ring,
$R_4$ and $R_5$ form a divalent moiety of wherein $R_8$ is hydrogen or alkyl;
each of l and m is independently an integer selected from 2 to 4; and
p is an integer of 0 or 1,
or a pharmaceutically acceptable salt thereof

2. The method of claim 1, wherein said disorder is an ischemic or hemorrhagic stroke.

3. The method of claim 1, wherein said disorder is Alzheimer's disease.

4. The method of claim 1, wherein said disorder is epilepsy.

5. The method of claim 1, wherein:
$R_1$ is hydrogen;
each of $R_2$ and $R_3$ is independently selected from hydrogen, $C_{1-6}$ alkyl, $-COR_6$, $-SO_2R_7$, or substituted or unsubstituted phenyl or benzyl, wherein $R_6$ is alkyl, alkoxy, phenyl, phenyloxy or benzyloxy, each of which is unsubstituted or substituted with halogen, hydroxy, methoxy, ethoxy or nitro, and $R_7$ is unsubstituted or substituted lower alkyl or aryl;
A is $-(CH_2)_n$-or $-CH_2CH=CHCH_2-$, wherein n is an integer selected from 2 to 4;
$R_4$ is hydrogen and $R_5$ is hydrogen or benzoyl unsubstituted or substituted with one or more of halogen, hydroxy, alkoxy or nitro in benzene ring, or when $R_4$ and $R_5$ together with N form a ring, R₄ and R₅ form a divalent moiety of wherein R₈ is hydrogen or alkyl;
each of l and m is independently an integer selected from 2 to 4; and
p is an integer of 0 or 1.

6. The method of claim 1 wherein the compound is selected from the group consisting of:
- 3-{3-[4-(3-aminopropylamino)butylamino]propyl}-1H-quinazoline-2,4-dione;
- 3-(3-{4-[3-(2,4-dioxo-1,4-dihydro-2H-quinazolin-3-yl)propylamino]butylamino}propyl)-1H-quinazoline-2,4-dione;
- N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}acetamide;
- N-(4-{acetyl-[3-(2,4-dioxo-1,4-dihydro-2H-quinazolin-3-yl)propyl]amino}butyl)-N-[3-(2,4-dioxo-1,4-dihydro-2H-quinazolin-3-yl)propyl]acetamide;
- [3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid ethyl ester;
- N-[3-(2,4-dioxo-1,4-dihydro-2H-quinazolin-3-yl)propyl]-N-(4-{[3-(2,4-dioxo-1,4-dihydro-2H-quinazolin-3-yl)propyl]methylamino}butyl)acetamide;
- 3-{4-[3-(2,4-dioxo-1,4-dihydro-2H-quinazolin-3-yl)propylamino]butyl}-1H-quinazoline-2,4-dione;
- N-(3-{4-[3-(2,4-dioxo-1,4-dihydro-2H-quinazolin-3-yl)propylamino]butylamino}propyl)-4-hydroxybenzamide;
- 3-{3-[4-({N-[3-(2,4-dioxo-1,4-dihydro-2H-quinazolin-3-yl)propyl]-N-benzyl}amino)butyl amino]propyl}-1H-quinazoline-2,4-dione;
- N-[3-(2,4-dioxo-1,4-dihydro-2H-quinazolin-3-yl)propyl]-N-{4-[3-(2,4-dioxo-1,4-dihydro-2H- quinazolin-3-yl)propylamino]butyl}benzamide;
- [3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid tert-butyl ester;
- N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}methansulfonamide;
- N-(4-{benzyl-[3-(2,4-dioxo-1,4-dihydro-2H-quinazolin-3-yl)propyl]amino}butyl)-N-[3-(2,4-dioxo-1,4-dihydro-2H-quinazolin-3-yl)propyl]acetamide;
- (4-{acetyl-[3-(2,4-dioxo-1,4-dihydro-2H-quinazolin-3-yl)propyl]amino}butyl)-[3-(2,4-dioxo-1,4-dihydro-2H-quinazolin-3-yl)propyl]carbamic acid ethyl ester;
- 3-{[3-(4-{N-[3-(2,4-dioxo-1,4-dihydro-2H-quinazolin-3-yl)propyl]-N-benzylamino}butyl)-N-benzylamino]propyl}-1H-quinazoline-2,4-dione;
- [3-(2,4-dioxo-1,4-dihydro-2H-quinazolin-3-yl)propyl]-(4-{[3-(2,4-dioxo-1,4-dihydro-2H-quinazolin-3-yl)propyl]ethoxycarbonylamino}butyl)carbamic acid ethyl ester;
- (4-{tert-butoxycarbonyl-[3-(2,4-dioxo-1,4-dihydro-2H-quinazolin-3-yl)propyl]amino}butyl)-[3-(2,4-dioxo-1,4-dihydro-2H-quinazolin-3-yl)propyl]carbamic acid tert-butyl ester;
- N-[3-(2,4-dioxo-1,4-dihydro-2H-quinazolin-3-yl)propyl]-N-(4-{[3-(2,4-dioxo-1,4-dihydro-2H-quinazolin-3-yl)propyl]methansulfonylamino}butyl)methansulfonamide;
- N-[3-(acetyl-{4-[3-(2,4-dioxo-1,4-dihydro-2H-quinazolin-3-yl)propylamino]butyl}amino) propyl]-4-hydroxybenzamide;
- N-[3-(4-{acetyl-[3-(2,4-dioxo-1,4-dihydro-2H-quinazolin-3-yl)propyl]amino}butylamino) propyl]-4-hydroxybenzamide;
- N-{3-[acetyl-(4-{acetyl-[3-(2,4-dioxo-1,4-dihydro-2H-quinazolin-3-yl)propyl]amino}butyl) amino]propyl}-4-hydroxybenzamide;
- N-[4-(2,4-dioxo-1,4-dihydro-2H-quinazolin-3-yl)butyl]-N-[3-(2,4-dioxo-1,4-dihydro-2H- quinazolin-3-yl)propyl]acetamide;
- 3-(2-{3-[2-(2,4-dioxo-1,4-dihydro-2H-quinazolin-3-yl)ethylamino]propylamino }ethyl)-1H-quinazoline-2,4-dione;
- 3-(3-{3-[3-(2,4-dioxo-1,4-dihydro-2H-quinazolin-3-yl)propylamino]propylamino}propyl)-1H-quinazoline-2,4-dione;
- 3-(3-{4-[3-(2,4-dioxo-1,4-dihydro-2H-quinazolin-3-yl)propylamino]-2-butenylamino}propyl)-1H-quinazoline-2,4-dione;
- (4-{tert-butoxycarbonyl-[3-(1-methyl-2,4-dioxo-1,4-dihydro-2H-quinazolin-3-yl)propyl]amino}butyl)-[3-(1-methyl-2,4-dioxo-1,4-dihydro-2H-quinazolin-3-yl)propyl]carbamic acid tert-butyl ester;
- 1-methyl-3-(3-{4-[3-(1-methyl-2,4-dioxo-1,4-dihydro-2H-quinazolin-3-yl) propylamino]butylamino}propyl)-1H-quinazoline-2,4-dione;
- 3-(3-{4-[3-(1,3-dioxo-1,3-dihydro-isoindole-2-yl)propylamino]butylamino}propyl)-1H-quinazoline-2,4-dione;
- 3-(3-{2-[3-(2,4-dioxo-1,4-dihydro-2H-quinazolin-3-yl)propylamino]ethylamino}propyl)-1H-quinazoline-2,4-dione;
- [3-(2,4-dioxo-1,4-dihydro-2H-quinazolin-3-yl)propyl]-(4-{[3-(2,4-dioxo-1,4-dihydro-2H-quinazolin-3-yl)propyl]hexylamino}butyl)carbamic acid tert-butyl ester;
- 3-[3-(4-{N-[3-(2,4-dioxo-1,4-dihydro-2H-quinazolin-3-yl)propyl]-N-hexylamino}butylamino)propyl]-1H-quinazoline-2,4-dione;
- (4-{tert-butoxycarbonyl-3-(1-hexyl-2,4-dioxo-1,4-dihydro-2H-quinazolin-3-yl)propyl]amino}butyl)-3-(1-hexyl-2,4-dioxo-1,4-dihydro-2H-quinazolin-3-yl)propyl]carbamic acid tert-butyl ester;
- 1-hexyl-3-(3-{4-[3-(1-hexyl-2,4-dioxo-1,4-dihydro-2H-quinazolin-3-yl) propylamino]butylamino}propyl)-1H-quinazoline-2,4-dione;
- [3-(2,4-dioxo-1,4-dihydro-2H-quinazolin-3-yl)propyl]-(4-{[3-(2,4-dioxo-1,4-dihydro-2H-quinazolin-3-yl)propyl]heptanoylamino}butyl)carbamic acid tert-butyl ester;
- [3-(2,4-dioxo-1,4-dihydro-2H-quinazolin-3-yl)propyl]-{4-[3-(2,4-dioxo-1,4-dihydro-2H-quinazolin-3-yl)propylamino]butyl}heptanoic amide;
- N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-2,2,2-trifluoroacetamide;
- N-[3-(2,4-dioxo-1,4-dihydro-2H-quinazolin-3-yl)propyl]-N-{4-[[3-(2,4-dioxo-1,4-dihydro-2H-quinazolin-3-yl)propyl]-(2,2,2-trifluoroacetyl)amino]butyl}-2,2,2-trifluoroacetamide;

N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-2-methoxyacetamide;

[3-(2,4-dioxo-1,4-dihydro-2H-quinazolin-3-yl)propyl]-{4-[3-(2,4-dioxo-1,4-dihydro-2H-quinazolin-3-yl)propylamino]butyl}carbamic acid benzyl ester;

N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-4-methylbenzenesulfonamide;

N-[3-(2,4-dioxo-1,4-dihydro-2H-quinazolin-3-yl)propyl]-N-(4-{[3-(2,4-dioxo-1,4-dihydro-2H-quinazolin-3-yl)propyl]-4-methylbenzenesulfonylamino }butyl)-4-methylbenzenesulfonamide; and 3-(3-{4 [3-(2,5-dioxo-pyrrolidine-1-yl)propylamino]butylamino }propyl)-1H-quinazoline-2,4-dione, or a pharmaceutically acceptable salt thereof

7. The method of claim 1 wherein the compound is N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}acetamide, or a pharmaceutically acceptable salt thereof.

8. The method of claim 1 wherein the compound is 3-{4-[3-(2,4-dioxo-1,4 -dihydro-2H-quinazolin-3-yl)propylamino]butyl}-1H-quinazoline-2,4-dione, or a pharmaceutically acceptable salt thereof.

9. The method of claim 1 wherein the compound is 3-{3 [4-({N-[3-(2,4-dioxo-1,4-dihydro-2H-quinazolin-3-yl)propyl]-N-benzyl}amino)butylamino]propyl}-1H- quinazoline-2,4-dione, or a pharmaceutically acceptable salt thereof.

10. The method of claim 1 wherein the compound is N-[3-(acetyl-{4-[3-(2,4-dioxo-1,4-dihydro-2H-quinazolin-3-yl)propylamino]butyl}amino)propyl]-4-hydroxybenzamide, or a pharmaceutically acceptable salt thereof

11. The method of claim 1 wherein the compound is N-[3-(4-{acetyl-[3-(2,4-dioxo-1,4-dihydro-2H-quinazolin-3-yl)propyl]amino}butylamino)propyl]-4-hydroxybenzamide, or a pharmaceutically acceptable salt thereof.

12. The method of claim 1 wherein the compound is 3-(2-{3-[2-(2,4-dioxo-1,4-dihydro-2H-quinazolin-3-yl)ethylamino]propylamino}ethyl)-1H-quinazoline-2,4-dione, or a pharmaceutically acceptable salt thereof.

13. The method of claim 1 wherein the compound is [3-(2, 4-dioxo-1,4-dihydro-2H-quinazolin-3-yl)propyl]-(4-{[3-(2, 4-dioxo-1,4-dihydro-2H-quinazolin-3-yl)propyl]hexylamino} butyl) carbamic acid tert-butyl ester, or a pharmaceutically acceptable salt thereof.

14. The method of claim 1 wherein the compound is [3-(2, 4-dioxo-1,4-dihydro-2H-quinazolin-3-yl)propyl]-{4-[3-(2, 4-dioxo-1,4-dihydro-2H-quinazolin-3-yl)propylamino] butyl}carbamic acid benzyl ester, or a pharmaceutically acceptable salt thereof.

15. The method of claim 1 wherein the compound is N-[3-(2,4-dioxo-1,4-dihydro-2H-quinazolin-3-yl)propyl]-N-{4-[3-(2,4-dioxo-1,4-dihydro-2H-quinazolin-3-yl)propylamino]butyl}-4-methylbenzenesulfonamide, or a pharmaceutically acceptable salt thereof.

* * * * *